United States Patent
Schohe-Loop et al.

(10) Patent No.: US 7,569,563 B2
(45) Date of Patent: Aug. 4, 2009

(54) SUBSTITUTED QUINOLONES II

(75) Inventors: Rudolf Schohe-Loop, Wuppertal (DE); Holger Zimmermann, Wuppertal (DE); Kerstin Henninger, Wuppertal (DE); Dieter Lang, Velbert (DE); Kai Thede, Berlin (DE); Chantal Fuerstner, Muelheim An Der Ruhr (DE); David Brueckner, Essen (DE)

(73) Assignee: AiCuris GmbH & Co. HK, Wuppertal (DE)

( * ) Notice: Subject to any disclaimer, the term of this patent is extended or adjusted under 35 U.S.C. 154(b) by 0 days.

(21) Appl. No.: 12/006,086

(22) Filed: Dec. 28, 2007

(65) Prior Publication Data

US 2008/0261964 A1  Oct. 23, 2008

Related U.S. Application Data

(63) Continuation of application No. PCT/EP2006/006197, filed on Jun. 27, 2006.

(30) Foreign Application Priority Data

Jun. 30, 2005 (DE) .................. 10 2005 030 524

(51) Int. Cl.
*A61K 31/5365* (2006.01)
*A61K 31/496* (2006.01)
*C07D 215/56* (2006.01)
*C07D 498/061* (2006.01)
*A61K 31/551* (2006.01)

(52) U.S. Cl. ............... 514/218; 514/253.08; 514/230.2; 544/101; 544/363; 540/575

(58) Field of Classification Search ............... None
See application file for complete search history.

(56) References Cited

U.S. PATENT DOCUMENTS

| | | |
|---|---|---|
| 4,908,366 A | 3/1990 | Schriewer et al. |
| 4,959,363 A | 9/1990 | Wentland |
| 5,051,418 A | 9/1991 | Schriewer et al. |

| | | |
|---|---|---|
| 2007/0293478 A1* | 12/2007 | Zimmermann et al. ...... 514/218 |

FOREIGN PATENT DOCUMENTS

| | | |
|---|---|---|
| CA | 2115021 | 8/1994 |
| EP | 0241206 | 10/1987 |
| EP | 0276700 | 8/1988 |
| EP | 0612731 | 8/1994 |
| WO | WO-97/04775 | 2/1997 |
| WO | WO-97/04779 | 2/1997 |
| WO | WO-00/40561 | 7/2000 |
| WO | WO-02/09758 | 2/2002 |
| WO | WO-02/26713 | 4/2002 |
| WO | WO-02/085886 | 10/2002 |
| WO | WO-03/050107 | 6/2003 |
| WO | WO-2006/008046 | 1/2006 |
| WO | WO-2007/003308 | 1/2007 |

OTHER PUBLICATIONS

Drug Evaluations by American Medical Association (6th Ed.), pp. 1615-1627 (1986).*
Chong et al., Abstract of 39th Interscience Conference on Antimicrobial Agents and Chemotherapy, 1999, p. 439.
Cinatl Jr. et al., FEMS Microbiology Reviews (2004) 28:59-77.
Da Silva et al., Current Medicinal Chemistry (2003) 10:21-39.
Sanchez et al., J. Med. Chem. (1995) 38:4478-4487.

* cited by examiner

*Primary Examiner*—Emily Bernhardt
(74) *Attorney, Agent, or Firm*—Marshall, Gerstein & Borun LLP

(57) ABSTRACT

The invention relates to substituted quinolones of formula (I) and to methods for their preparation as well as their use for the production of medicaments for the treatment and/or prophylaxis of diseases, especially for use as antiviral agents, in particular against cytomegaloviruses.

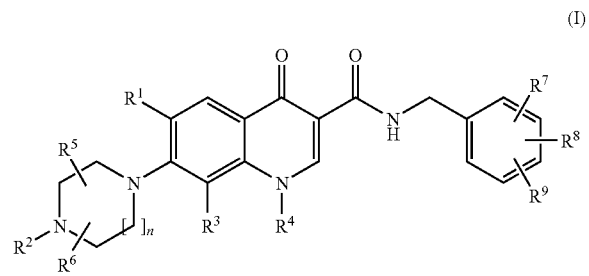

11 Claims, No Drawings

SUBSTITUTED QUINOLONES II

CROSS REFERENCE TO RELATED APPLICATIONS

This application is a continuation of pending international application PCT/EP2006/006197, filed Jun. 27, 2006, designating US, which claims priority from German patent application DE 10 2005 030 524.5, filed Jun. 30, 2005. The contents of the above-referenced applications are incorporated herein by this reference in their entirety.

BACKGROUND OF THE INVENTION

The invention relates to substituted quinolones and methods for their preparation as well as their use for the production of medicaments for the treatment and/or prophylaxis of diseases, especially for use as antiviral agents, in particular against cytomegaloviruses.

WO 00/040561 and U.S. Pat. No. 4,959,363 describe quinolones having activity against viruses of the herpes family. EP-A 612731 describes quinolones as antiviral agents, particularly against HIV. WO 02/009758, WO 02/085886 and WO 03/050107 claim quinolones as broad-spectrum antibiotics. WO 97/004775 and WO 97/004779 describe quinolones as inhibitors of PDE4 and TNFα, inter alia for the treatment of antiinflammatory diseases and HIV. EP-A 276700 describes 8-cyanoquinolones as antibiotics. WO 02/026713 describes quinolones as antiparasitic compounds.

On the market there are structurally different agents having antiviral activity, but their breadth of application is severely limited owing to a pronounced side-effect profile and a possible development of resistances. New agents for a better and more effective therapy are therefore desirable.

SUMMARY OF THE INVENTION

One object of the present invention is therefore to provide new compounds with equal or improved antiviral activity for the treatment of viral infectious diseases in humans and animals.

Surprisingly it has been found that the substituted quinolones described in the present invention have antiviral activity.

The invention relates to compounds of formula

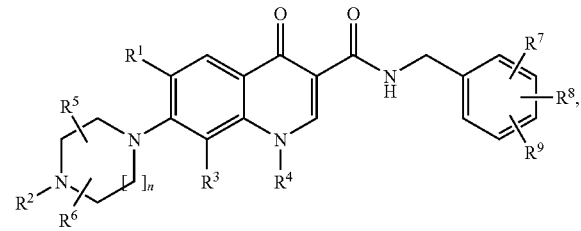

(I)

in which n represents a number 1 or 2, $R^1$ represents hydrogen, fluorine, chlorine or trifluoromethyl, $R^1$ represents $C_1$-$C_6$-alkyl, $C_1$-$C_6$-alkylaminocarbonyl or —C(=O)—$R^{10}$, whereby alkyl and alkylaminocarbonyl are substituted with a substituent, whereby the substituent is selected from the group consisting of hydroxycarbonyl and $C_1$-$C_6$-alkoxycarbonyl, and $R^{10}$ represents hydroxycarbonyl, $C_1$-$C_6$-alkoxycarbonyl, hydroxycarbonylmethyl or $C_1$-$C_6$-alkoxycarbonylmethyl, $R^3$ represents halogen, cyano, methoxy, trifluoromethyl, monofluoromethoxy, difluoromethoxy, trifluoromethoxy or ethynyl, $R^4$ represents $C_1$-$C_6$-alkyl or $C_3$-$C_8$-cycloalkyl, whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_6$-alkylamino, $C_1$-$C_6$-alkylcarbonyl and $C_1$-$C_6$-alkoxycarbonyl, and whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl, or $R^3$ and $R^4$, together with the atoms to which they are bonded, form a ring through a group of formula

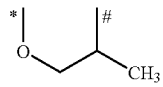

whereby

\* is the linkage site to the carbon atom, and

\# is the linkage site to the nitrogen atom, $R^5$ and $R^6$ independently of one another represent hydrogen, methyl or ethyl, $R^7$ and $R^8$ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy, $R^9$ represents hydrogen, halogen, hydroxy, cyano, trifluoromethyl, monofluoromethoxy, difluoromethoxy, trifluoromethoxy, $C_1$-$C_3$-alkyl or $C_1$-$C_3$-alkoxy, and their salts, their solvates and the solvates of their salts.

Compounds of the invention are the compounds of formula (I), (Ia) and (Ib) and their salts, solvates and solvates of the salts; the compounds of the formulae mentioned below, encompassed by formula (I), (Ia) and (Ib), and their salts, solvates and solvates of the salts as well as the compounds mentioned below as exemplary embodiments, encompassed by formula (I), (Ia) and (Ib), and their salts, solvates and solvates of the salts, insofar as the compounds mentioned below and encompassed by formula (I), (Ia) and (Ib) are not already salts, solvates and solvates of the salts.

The compounds of the invention may, depending on their structure, exist in stereoisomeric forms (enantiomers, diastereomers). The invention therefore relates to the enantiomers or diastereomers and their respective mixtures. The stereoisomerically uniform constituents can be isolated from such mixtures of enantiomers and/or diastereomers in a known way.

Where the compounds of the invention can occur in tautomeric forms, the present invention encompasses all of the tautomeric forms.

Salts preferred for the purposes of the present invention are physiologically acceptable salts of the compounds of the invention. Also encompassed, however, are salts which themselves are not suitable for pharmaceutical applications, but can nevertheless be used, for example, for the isolation or purification of the compounds of the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of usual bases, such as, by way of example and preferably, alkali metal salts (e.g. sodium and potassium salts), alkaline earth metal salts (e.g. calcium and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates for the purposes of the invention refer to those forms of the compounds of the invention which in solid or liquid state form a complex through coordination with solvent molecules. Hydrates are a special form of the solvates, in which the coordination takes place with water.

In the context of the present invention, the substituents have the following meaning unless stated otherwise:

Alkyl per se and "alk" and "alkyl" in alkoxy, alkylamino, alkylcarbonyl, alkoxycarbonyl and alkylaminocarbonyl represent a linear or branched alkyl radical generally having 1 to 6, preferably 1 to 4, particularly preferably 1 to 3 carbon atoms, by way of example and preferably methyl, ethyl, n-propyl, isopropyl, tert-butyl, n-pentyl and n-hexyl.

Alkoxy by way of example and preferably represents methoxy, ethoxy, n-propoxy, isopropoxy, tert-butoxy, n-pentoxy and n-hexoxy.

Alkylamino represents an alkylamino radical having one or two alkyl substituents (selected independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. $C_1$-$C_3$-Alkylamino for example represents a monoalkylamino radical having 1 to 3 carbon atoms or a dialkylamino radical having 1 to 3 carbon atoms each per alkyl substituent.

Alkylcarbonyl by way of example and preferably represents acetyl and propanoyl.

Alkoxycarbonyl by way of example and preferably represents methoxycarbonyl, ethoxycarbonyl, n-propoxycarbonyl, isopropoxycarbonyl, tert-butoxycarbonyl, n-pentoxycarbonyl and n-hexoxycarbonyl.

Alkylaminocarbonyl represents an alkylaminocarbonyl radical having one or two alkyl substituents (selected independently of one another), by way of example and preferably methylaminocarbonyl, ethylaminocarbonyl, n-propylaminocarbonyl, isopropylaminocarbonyl, tert-butylaminocarbonyl, n-pentylaminocarbonyl, n-hexylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl, N-tert-butyl-N-methylaminocarbonyl, N-ethyl-N-n-pentylaminocarbonyl and N-n-hexyl-Nmethylaminocarbonyl. $C_1$-$C_3$-Alkylaminocarbonyl for example represents a monoalkylaminocarbonyl radical having 1 to 3 carbon atoms or a dialkylaminocarbonyl radical having 1 to 3 carbon atoms each per alkyl substituent.

Cycloalkyl represents a cycloalkyl group generally having 3 to 8, preferably 3 to 5 carbon atoms, preferred examples which can be named for of cycloalkyl include cyclopropyl, cyclobutyl, cyclopentyl, cyclohexyl and cycloheptyl.

Halogen represents fluorine, chlorine, bromine and iodine, preferably fluorine and chlorine.

In the formula of the group which $R^3$ and $R^4$ can represent, the end point of the line adjacent to which there is in each case an * or # is not a carbon atom or a $CH_2$ group but rather a component of the bond to the atom to which $R^3$ and $R^4$ are bonded.

Preference is given to those compounds of formula (I) which correspond to formula

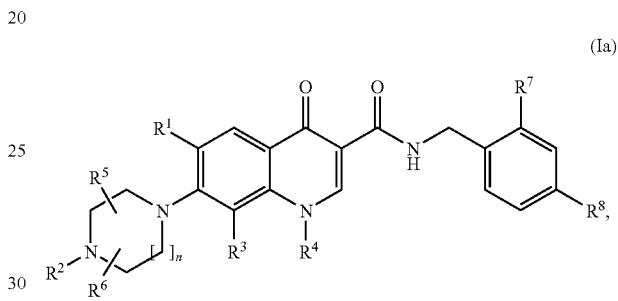

(Ia)

in which
n represents the number 1,
$R^1$ represents hydrogen or fluorine,
$R^2$ represents $C_1$-$C_4$-alkyl,
  whereby alkyl is substituted with a substituent, whereby the substituent is selected from the group consisting of hydroxycarbonyl and $C_1$-$C_6$-alkoxycarbonyl,
$R^3$ represents fluorine, chlorine, trifluoromethyl, methoxy, monofluoromethoxy, difluoromethoxy, trifluoromethoxy or ethynyl,
$R^4$ represents $C_1$-$C_4$-alkyl or $C_3$-$C_5$-cycloalkyl,
  whereby alkyl can be substituted with 1 to 3 substituents, whereby the substituents are selected independently of one another from the group consisting of fluorine, hydroxy and $C_1$-$C_3$-alkoxy,
  and
  whereby cycloalkyl can be substituted with 1 to 3 substituents, whereby the substituents are selected independently of one another from the group consisting of halogen, hydroxy, trifluoromethyl, $C_1$-$C_3$-alkyl and $C_1$-$C_3$-alkoxy,
or
$R^3$ and $R^4$, together with the atoms to which they are bonded, form a ring through a group of formula

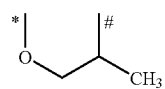

whereby
* is the linkage site to the carbon atom,
and
is the linkage site to the nitrogen atom, $R^5$ and $R^6$ independently of one another represent hydrogen or methyl, $R^7$ and $R^8$ independently of one another represent fluorine, chlorine, cyano, trifluoromethyl, difluoromethoxy, trifluoromethoxy, $C_1$-$C_3$-alkyl or $C_1$-$C_3$-alkoxy, and their salts, their solvates and the solvates of their salts.

Particular preference is given to those compounds of formula (I) or (Ia), which correspond to formula

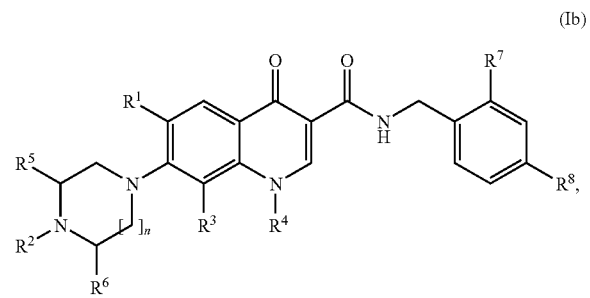

(Ib)

in which
n represents the number 1,
$R^1$ represents fluorine,
$R^2$ represents methyl or ethyl,
    whereby methyl and ethyl are substituted with a substituent, whereby the substituent is selected from the group consisting of hydroxycarbonyl, methoxycarbonyl and ethoxycarbonyl,
$R^3$ represents chlorine, methoxy, difluoromethoxy or trifluoromethoxy,
$R^4$ represents methyl, ethyl or cyclopropyl,
    whereby ethyl can be substituted with 1 to 3 fluorine substituents,
    and
    whereby cyclopropyl can be substituted with 1 to 2 fluorine substituents,
or
$R^3$ and $R^4$, together with the atoms to which they are bonded, form a ring through a group of formula

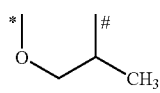

whereby
* is the linkage site to the carbon atom,
and
\# is the linkage site to the nitrogen atom,
$R^5$ and $R^6$ independently of one another represent hydrogen or methyl,
$R^7$ and $R^8$ independently of one another represent chlorine, trifluoromethyl, trifluoromethoxy or methyl,
and their salts, their solvates and the solvates of their salts.

Preference is also given to those compounds of formula (I), (Ia) and (Ib), in which $R^1$ represents fluorine.

Preference is also given to those compounds of formula (I), (Ia) and (Ib) in which $R^2$ represents methylene, whereby methylene is substituted with a substituent, whereby the substituent is selected from the group consisting of hydroxycarbonyl, methoxycarbonyl and ethoxycarbonyl.

Preference is also given to those compounds of formula (I), (Ia) and (Ib) in which $R^3$ represents chlorine, methoxy or difluoromethoxy.

Preference is also given to those compounds of formula (I), (Ia) and (Ib) in which $R^4$ represents cyclopropyl or 2-fluorocycloprop-1-yl.

Preference is also given to those compounds of formula (I), (Ia) and (Ib) in which $R^4$ represents 2,2,2-trifluoroethyl.

Preference is also given to those compounds of formula (I), (Ia) and (Ib) in which $R^7$ and $R^8$ represent chlorine.

Preference is also given to those compounds of formula (I), (Ia) and (Ib) in which $R^7$ represents chlorine or methyl and $R^8$ represents trifluoromethyl or trifluoromethoxy.

Preference is also given to those compounds of formula (I) in which $R^9$ represents hydrogen.

The radical definitions stated specifically in the respective combinations and preferred combinations of radicals are also replaced as desired by radical definitions of another combination, irrespective of the particular combination of the radicals specified.

Very particular preference is given to combinations of two or more of the abovementioned preference ranges.

The invention further relates to a method for preparing the compounds of formula (I), whereby compounds of formula

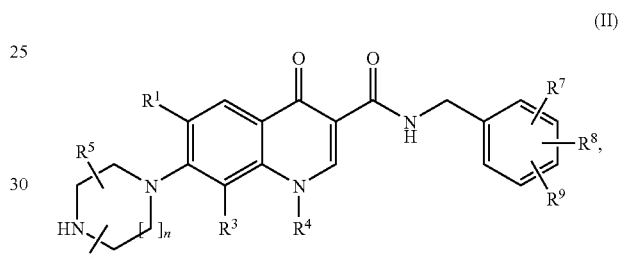

(II)

in which
n, $R^1$, $R^3$, $R^4$, $R^5$, $R^6$, $R^7$, $R^8$ and $R^9$ have the meaning indicated above,
are reacted,
according to method [A], with compounds of formula $$R^2-X^1 \quad (III),$$

in which
$R^2$ represents $C_1$-$C_6$-alkyl,
    whereby alkyl is substituted with a $C_1$-$C_6$-alkoxycarbonyl substituent,
and
$X^1$ represents halogen, preferably iodine, chlorine or bromine, or mesylate, tosylate or triflate,
or
according to method [B], with compounds of formula $$R^{2a}-NCO \quad (IV),$$

in which
$R^{2a}$ represents the alkyl of the alkylaminocarbonyl of the radical $R^2$,
    whereby alkylaminocarbonyl is substituted with a $C_1$-$C_6$-alkoxycarbonyl substituent,
or
according to method [C], with compounds of formula

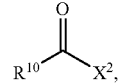

(V)

in which

R¹⁰ has the meaning indicated above, and

X² represents halogen, preferably chlorine or bromine, or whereby compounds formed by the reaction of compounds of formula (II) with compounds of formulae (III) or (IV) are hydrolysed, according to method [D], with a base to form the corresponding acid.

The reaction according to method [A] generally takes place in inert solvents, in the presence of a base, preferably in a temperature range from −30° C. to 120° C. under atmospheric pressure.

Examples of inert solvents include halohydrocarbons such as dichloromethane or trichloromethane, hydrocarbon such as benzene, or other solvents such as nitromethane, dioxane, dimethylformamide or acetonitrile. It is likewise possible to use mixtures of the solvents. Acetonitrile, dichloromethane or dimethylformamide is particularly preferred.

Examples of bases include alkali metal carbonates, such as for example sodium or potassium carbonate, or sodium or potassium hydrogen carbonate, or organic bases such as trialkylamines, for example triethylamine, N-methylmorpholine, N-methylpiperidine, 4-dimethylaminopyridine or diisopropylethylamine.

The reaction according to method [B] generally takes place in inert solvents, preferably in a temperature range from −30° C. to 50° C. under atmospheric pressure.

Examples of inert solvents include halohydrocarbons such as dichloromethane or trichloromethane, hydrocarbon such as benzene, or other solvents such as nitromethane, dioxane, dimethylformamide or acetonitrile. It is likewise possible to use mixtures of the solvents. Dichloromethane or dimethylformamide is particularly preferred.

The reaction according to method [C] generally takes place in inert solvents, where appropriate in the presence of a base, preferably in a temperature range from −30° C. to 50° C. under atmospheric pressure.

Examples of inert solvents include halohydrocarbons such as dichloromethane or trichloromethane, hydrocarbon such as benzene, or other solvents such as nitromethane, dioxane, dimethylformamide or acetonitrile. It is likewise possible to use mixtures of the solvents. Dichloromethane or dimethylformamide is particularly preferred.

Examples of bases include alkali metal carbonates, such as for example sodium or potassium carbonate, or sodium or potassium hydrogen carbonate, or organic bases such as pyridine or trialkylamines, for example triethylamine, N-methylmorpholine, N-methylpiperidine, 4-dimethylaminopyridine or diisopropylethylamine.

The hydrolysis according to method [D] generally takes place in water or inert solvents or in mixtures of water and inert solvents, in the presence of a base, preferably in a temperature range from −30° C. to 100° C. under atmospheric pressure.

Examples of inert solvents include halohydrocarbons such as dichloromethane or trichloromethane, hydrocarbon such as benzene, or other solvents such as nitromethane, dioxane, methanol, tetrahydrofuran, dimethylformamide or acetonitrile. It is likewise possible to use mixtures of the solvents. Dioxane, methanol, tetrahydrofuran or dimethylformamide is particularly preferred.

Examples of bases include alkali metal hydroxides or alkali metal carbonates, such as for example sodium, potassium or lithium hydroxide, sodium or potassium carbonate or sodium or potassium hydrogen carbonate.

The compounds of formulae (III), (IV) and (V) are known or can be synthesized by known methods from the corresponding starting materials.

The compounds of formula (I), in which R² represents a substituted ethyl, can also be prepared by reacting the compounds of formula (II) with a Michael-acceptor, such as, for example, ethyl acrylate.

The compounds of formula (II) are known or can be prepared by reacting compounds of formula in which

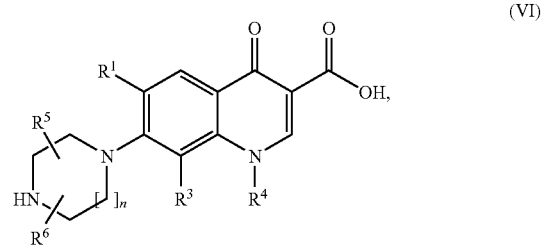

(VI)

n, R¹, R³, R⁴, R⁵ and R⁶ have the meaning indicated above, with compounds of formula

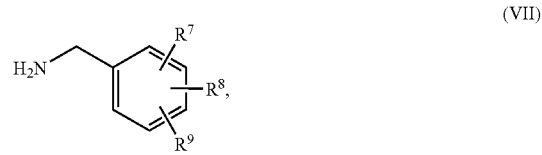

(VII)

in which

R⁷, R⁸ and R⁹ have the meaning indicated above.

The reaction generally takes place in inert solvents, in the presence of a dehydrating reagent, where appropriate in the presence of a base, preferably in a temperature range from −30° C. to 50° C. under atmospheric pressure.

Examples of inert solvents include halohydrocarbons such as dichloromethane or trichloromethane, hydrocarbon such as benzene, nitromethane, dioxane, dimethylformamide or acetonitrile. It is likewise possible to use mixtures of the solvents. Dichloromethane or dimethylformamide is particularly preferred.

Examples of bases include alkali metal carbonates, such as for example sodium or potassium carbonate, or sodium or potassium hydrogen carbonate, or organic bases such as trialkylamines, for example triethylamine, N-methylmorpholine, N-methylpiperidine, 4-dimethylaminopyridine or diisopropylethylamine.

Examples of dehydrating reagents suitable hereby include carbodiimides such as for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N-propyloxymethyl-polystyrene (PS-carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride, or O-(benzzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt) or benzotriazol-1-yloxytris(dimethylamino)phosphonium hexafluorophosphate BOP), or benzotriazol-1-yloxytris(pyrrolidino)phosphonium hexafluorophosphate (PyBOP), or N-hydroxysuccinimide, or mixtures of these, with bases.

Preferably the condensation is carried out with HATU, benzotriazol-1-yloxytris(pyrrolidino)phosphonium hexafluorophosphate (PyBOP) or with EDC in the presence of HOBt.

The compounds of formula (VII) are known or can be synthesized by known methods from the corresponding starting materials.

The compounds of formula (VI) are known or can be prepared by reacting compounds of formula

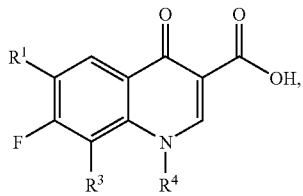
(VIII)

in which
$R^1$, $R^3$ and $R^4$ have the meaning indicated above, with compounds of formula

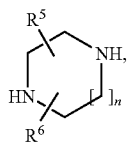
(IX)

in which
n, $R^5$ and $R^6$ have the meaning indicated above.

The reaction can be carried out by the methods described in A. Da Silva, M. De Almeida, V. De Souza, M. Couri, Current Medicinal Chemistry, 2003, 10, 21-39.

In the reaction of the compounds of formula (VIII) with compounds of formula (IX) one of the nitrogen atoms is optionally protected with a protecting group, such as for example, Fmoc or Boc, which is removed after the reaction in accordance with conditions known to a person skilled in the art.

The compounds of formula (VIII) are known or can be synthesized by known methods from the corresponding starting materials, as described for example in A. Da Silva, M. De Almeida, V. De Souza, M. Couri, *Current Medicinal Chemistry,* 2003, 10, 21-39.

The compounds of formula (IX) are known or can be synthesized by known methods from the corresponding starting materials.

In an alternative method, in order to prepare the compounds of formula (II), the nucleophilic substitution at the 7-position of the quinolone and the amide formation may be switched in the order of the reaction.

The preparation of the compounds of the invention can be illustrated by the following synthesis scheme.

Synthesis scheme:

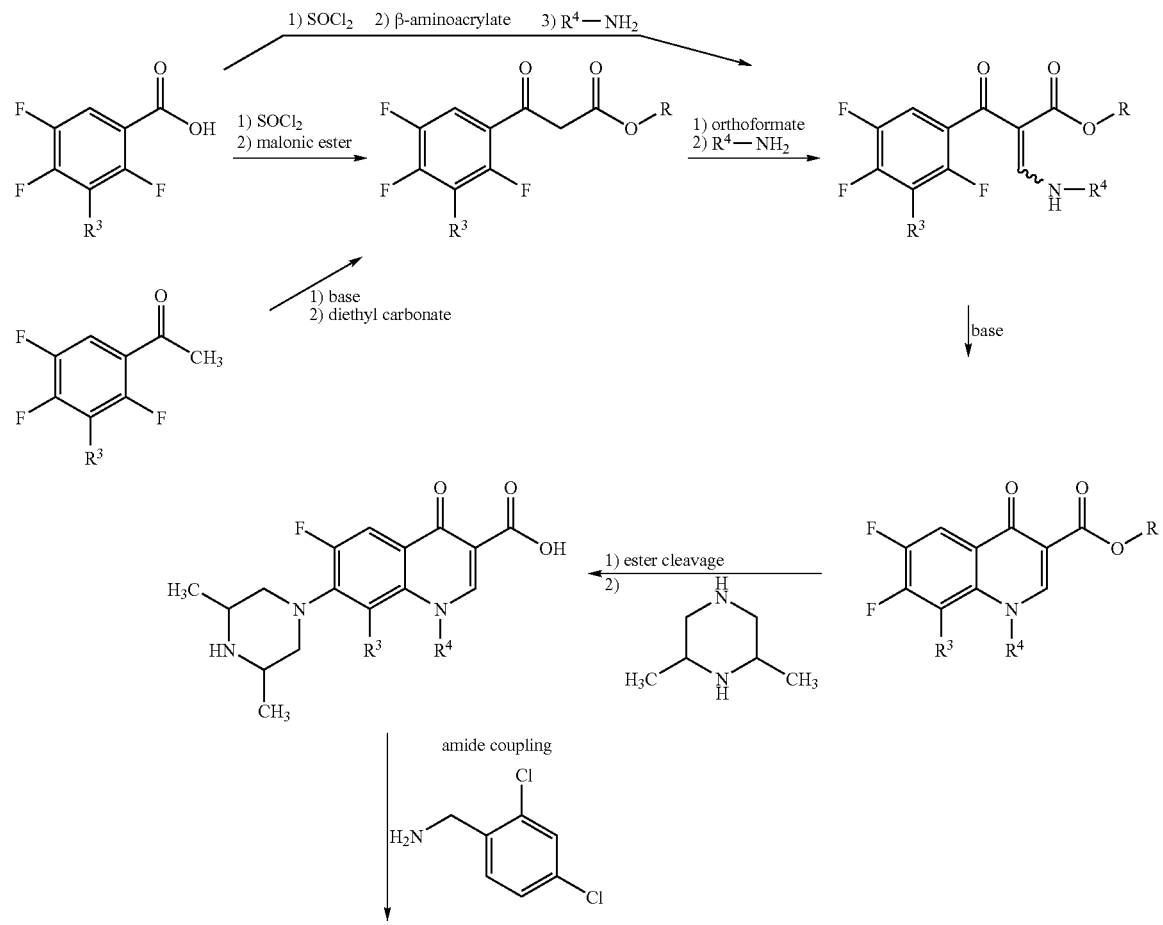

-continued

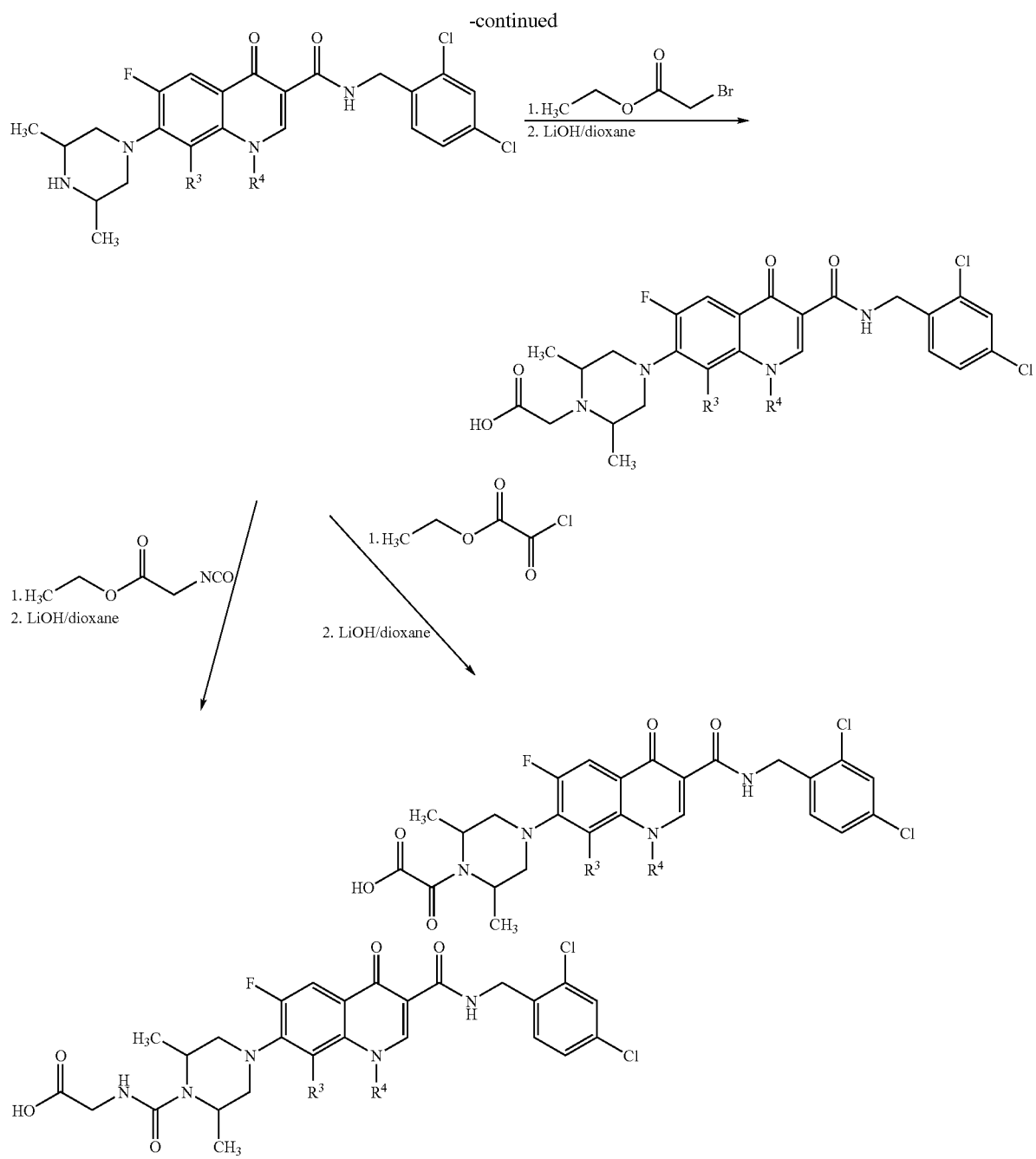

The compounds of the invention show a surprising spectrum of effects which could not have been predicted. They show an antiviral activity against representatives of the group of herpes viridae (herpes viruses), in particular against cytomegaloviruses (CMV) and especially against the human cytomegalovirus (HCMV).

Areas of indication which may be mentioned by way of example are:

1) Treatment and prophylaxis of HCMV infections in AIDS patients (retinitis, pneumonitis, gastrointestinal infections).
2) Treatment and prophylaxis of cytomegalovirus infections in bone-marrow and organ transplant patients who develop often life-threatening HCMV pneumonitis or encephalitis, as well as gastrointestinal and systemic HCMV infections.
3) Treatment and prophylaxis of HCMV infections in neonates and infants.
4) Treatment of an acute HCMV infection in pregnant women.
5) Treatment of an HCMV infection in immunosuppressed patients associated with cancer and cancer therapy.
6) Treatment of HCMV-positive cancer patients with the aim of reducing HCMV-mediated tumor progression (cf. J. Cinatl, et al., *FEMS Microbiology Reviews* 2004, 28, 59-77).

The present invention further relates to the use of the compounds of the invention for the treatment and/or prophylaxis of diseases, in particular of infections with viruses, especially the aforementioned viruses, and of the infectious diseases caused thereby. A viral infection hereinafter means both an infection with a virus and a disease caused by an infection with a virus.

The present invention further relates to the use of the compounds of the invention for the treatment and/or prophylaxis of diseases, especially of the aforementioned diseases.

The present invention further relates to the use of the compounds of the invention for the production of a medicament for the treatment and/or prophylaxis of diseases, especially of the aforementioned diseases.

The compounds of the invention are preferably used for the production of medicaments which are suitable for the prophylaxis and/or treatment of infections with a representative of the group of herpes viridae, particularly a cytomegalovirus, especially a human cytomegalovirus.

The present invention further relates to a method for the treatment and/or prophylaxis of diseases, especially the aforementioned diseases, using an antivirally effective amount of the compounds of the invention.

The present invention further relates to medicaments comprising at least one compound of the invention and at least one or more further active compounds, in particular for the treatment and/or prophylaxis of the aforementioned diseases. Suitable active compounds for the combination which may be mentioned by way of example, and preferably, are: antiviral active compounds such as valganciclovir, ganciclovir or aciclovir.

The compounds of the invention may act systemically and/or locally. For this purpose they can be administered in a suitable way, such as, for example, orally, parenterally, pulmonarily, nasally, sublingually, lingually, buccally, rectally, dermally, transdermally, conjunctivally, otically, topically, or as an implant or stent.

For these administration routes the compounds of the invention can be administered in suitable administration forms.

Suitable for oral administration are administration forms which function according to the prior art and deliver the compounds of the invention rapidly and/or in modified fashion and which comprise the compounds of the invention in crystalline and/or amorphicized and/or dissolved form, such as, for example, tablets (uncoated or coated tablets, for example having coatings which are resistant to gastric juice or dissolve with a delay or are insoluble and control the release of the compound of the invention), tablets or films/wafers, which disintegrate rapidly in the oral cavity, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenously, intraarterially, intracardially, intraspinally or intralumbarly) or with inclusion of absorption (e.g. intramuscularly, subcutaneously, intracutaneously, percutaneously, or intraperitoneally). Administration forms suitable for parenteral administration are, inter alia, preparations for injection and infusion in the form of solutions, suspensions, emulsions, lyophilisates or sterile powders.

Examples suitable for the other administration routes are pharmaceutical forms for inhalation (inter alia powder inhalers, nebulizers), nasal drops, solutions, sprays; tablets, films/wafers or capsules, to be administered lingually, sublingually or buccally, suppositories, preparations for ears or eyes, vaginal capsules, aqueous suspensions (lotions, shaking mixtures), lipophilic suspensions, ointments, creams, transdermal therapeutic systems, milk, pastes, foams, dusting powders, implants or stents.

The compounds of the invention can be converted into the stated administration forms. This can take place in a manner known per se by mixing with inert, non-toxic, pharmaceutically acceptable excipients. These excipients include, inter alia, carriers (for example microcrystalline cellulose, lactose, mannitol), solvents (for example liquid polyehylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (for example antioxidants such as for example ascorbic acid), colors (for example inorganic pigments such as for example iron oxides) or taste and/or odor corrigents.

The present invention further relates to medicaments which comprise at least one compound of the invention, usually together with one or more inert, non-toxic, pharmaceutically acceptable excipients, as well as their use for the aforementioned purposes.

It has generally proved advantageous to administer on intravenous administration of about 0.001 to 10 mg/kg, preferably about 0.01 to 5 mg/kg, of body weight to achieve effective results, and the dosage on oral administration is about 0.01 to 25 mg/kg, preferably 0.1 to 10 mg/kg, of body weight.

It may nevertheless be necessary where appropriate to deviate from the stated amounts, specifically as a function of body weight, administration route, individual response to the active compound, mode of preparation and time or interval over which administration takes place. Thus it may be sufficient in some cases to make do with less than the aforementioned minimum amount, whereas in other cases the stated upper limit must be exceeded. In the case of an administration of larger amounts it may be advisable to divide these into a plurality of individual doses over the day.

The percentage data in the following tests and examples are percentages by weight unless otherwise indicated; parts are parts by weight. Solvent ratios, dilution ratios and concentration data of liquid/liquid solutions are in each case based on volume.

DETAILED DESCRIPTION OF PREFERRED EMBODIMENTS

A. Examples

Abbreviations

Boc tert-butoxycarbonyl
$CDCl_3$ deuterochloroform
conc. concentrated
DCI direct chemical ionization (in MS)
DCM dichloromethane
DIEA N,N-diisopropylethylamine
DMSO dimethyl sulfoxide
DMF N,N-dimethylformamide
EDC N-(3-dimethylaminoisopropyl)-N'-ethylcarbodiimide hydrochloride
EE ethyl acetate
EI electron impact ionization (in MS)
ESI electrospray ionization (in MS)
Fmoc 9-fluorenylmethoxycarbonyl
h hour
HPLC high pressure, high performance liquid chromatography
HV high vacuum
LC-MS coupled liquid chromatography-mass spectroscopy
LDA lithium diisopropylamide min minutes
MS mass spectroscopy
MTBE methyl tert-butyl ether
NMR nuclear magnetic resonance spectroscopy
Pd—C palladium on carbon
PyBOP 1-benzotriazolyloxytripyrrolidinophosphonium hexafluorophosphate
RP-HPLC reverse phase HPLC
RT room temperature
$R_t$ retention time (in HPLC)
sat. saturated
THF tetrahydrofuran General LC-MS and HPLC Methods:

Method 1 (LC-MS): Instrument: Micromass Quattro LCZ with HPLC Agilent series 1100; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 mL/min, 2.5 min/3.0 min/4.5 min 2 mL/min; oven: 50° C.; UV detection: 208-400 nm.

Method 2 (LC-MS): MS instrument type: Micromass ZQ; HPLC instrument type: Waters Alliance 2795; column: Phenomenex Synergi 2μ Hydro-RP Mercury 20 mm×4 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 mL/min; oven: 50° C. UV detection: 210 nm.

Method 3 (LC-MS): MS instrument type: Micromass ZQ; HPLC instrument type: HP 1100 series; UV DAD; column: Phenomenex Synergi 2μ Hydro-RP Mercury 20 mm×4 mm; eluent A: 1 of water+0.5 ml of 50% formic acid, eluent B: 1 of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 4 (preparative HPLC): column: RP18; gradient with the addition of 0.2% diethylamine to the acetonitrile: 30% acetonitrile/70% water→95% acetonitrile/5% water.

Method 5 (preparative HPLC, formic acid): column: Grom-Sil 120 ODS-4HE, 10 μm, SNr. 3331, 250 mm×30 mm. Eluent A: formic acid 0.1% in water, eluent B: acetonitrile; flow rate: 50 ml/min. Program: 0-3 min: 10% B; 3-27 min: gradient to 95% B; 27-34 min: 95% B; 34.01-38 min: 10% B.

Method 6 (preparative HPLC, hydrochloric acid): column: Grom-Sil 120 ODS-4HE, 10 μm, SNr. 3331, 250 mm×30 mm. Eluent A: hydrochloric acid 0.1% in water, eluent B: acetonitrile; flow rate: 50 ml/min. Program: 0-2 min 10% B, 3-43 min: gradient to 100% B, 43.01-45 min: 100% B.

Method 7 (preparative HPLC): column: Grom-Sil 120 ODS-4HE, 10 μm, SNR. 3331, 250 mm×30 mm. Eluent A: water, eluent B: acetonitrile, flow rate: 50 ml/min. Program: 0-3 min: 10% B; 3-27 min: gradient to 95% B; 27-34 min: 95% B; 34.01-38 min: 10% B.

Method 8 (preparative HPLC, trifluoroacetic acid): column: Grom-Sil 120 ODS-4HE, 10 μm, SNr. 3331, 250 mm×30 mm. Eluent A: trifluoroacetic acid 0.1% in water, eluent B: acetonitrile. Flow rate: 50 ml/min. Program: 0-3 min: 10% B; 3-27 min: gradient to 95% B; 27-34 min: 95% B; 34.01-38 min: 10% B.

Method 9 (analytical HPLC): Instrument: HP 1100 with DAD detection; column: Kromasil 100 RP-18, 60 mm×2.1 mm, 3.5 μm; eluent A: 5 ml of perchloric acid (70%)/l of water, eluent B: acetonitrile; gradient: 0 min 2% B, 0.5 min 2% B, 4.5 min 90% B, 9 min 90% B, 9.2 min 2% B, 10 min 2% B; flow rate: 0.75 ml/min; column temperature: 30° C.; UV detection: 210 nm.

Method 10 (analytical HPLC): Instrument: HP 1100 with DAD detection; column: Kromasil 100 RP-18, 60 mm×2.1 mm, 3.5 μm; eluent A: 5 ml of perchloric acid (70%)/l of water, eluent B: acetonitrile; gradient: 0 min 2% B, 0.5 min 2% B, 4.5 min 90% B, 6.5 min 90% B, 6.7 min 2% B, 7.5 min 2% B; flow rate: 0.75 ml/min; column temperature: 30° C.; UV detection: 210 nm.

Method 11 (LC-MS): MS instrument type: Micromass ZQ; HPLC instrument type: Waters Alliance 2795; column: Merck Chromolith SpeedROD RP-18e 100 mm×4.6 mm; eluent A: water+0.5 ml of 50% formic acid/l; eluent B: acetonitrile+0.5 ml of 50% formic acid/l; gradient: 0.0 min 10% B→7.0 min 95% B→9.0 min 95% B; flow rate: 0.0 min 1.0 ml/min→7.0 min 2.0 ml/min→9.0 min 2.0 ml/min; oven: 35° C.; UV detection: 210 nm.

The example compounds which contain a basic nitrogen can be isolated as the free base or in various salt forms, depending on the purification method. The preparation method often describes the purification by HPLC with the addition of formic acid (method 5), which leads to the hydroformate, or with the addition of other acids, such as, for example, hydrochloric acid (method 6) instead of formic acid, whereby the product is isolated as the hydrochloride. Alternatively the product can also be purified by stirring it in acetonitrile or by preparative HPLC without the addition of acid (method 7), whereby the product is isolated as the free base. Both from the free base and from the hydroformate, the hydrochloride of the compound can be obtained again, by subsequent addition of hydrogen chloride in dioxane and evaporation on a rotary evaporator.

Starting Compounds

Example 1A

2-Bromo-4-chlorobenzonitrile

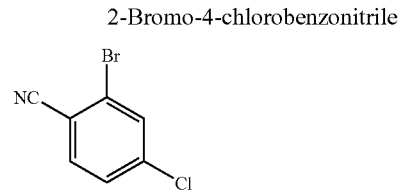

588 mg of 2-bromo-4-chlorobenzoic acid and 300 mg of urea are dissolved in dichloromethane/methanol and concentrated onto 364 mg of alumina on a rotary evaporator. The residue is irradiated in a microwave at 150° C. for a total of 60 min. After cooling, the residue is stirred with ethyl acetate and water, filtered, and the aqueous phase of the filtrate is separated. The organic phase is washed with a sodium hydrogen carbonate solution, dried over sodium sulfate, concentrated on a rotary evaporator and then dried under high vacuum. The product is reacted further without additional purification.

$^1$H NMR (300 MHz, CDCl$_3$): δ=7.72 (d, 1H), 7.60 (d, 1H), 7.42 (dd, 1H).

Example 2A

2-Chloro-4-(trifluoromethoxy)phenyl trifluoromethylsulfonate

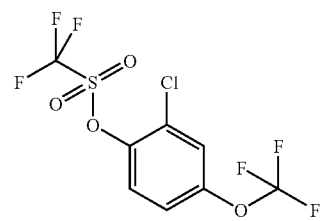

4.00 g of 2-chloro-4-trifluoromethoxyphenol in 50 ml of toluene and 50 ml of a 30% potassium phosphate solution in water are provided at 0° C., 3.82 ml of trifluoromethanesulfonic anhydride are slowly added, and the mixture is stirred at RT for 1.5 h. The aqueous phase is separated and the organic phase is washed with water, dried over sodium sulfate and concentrated. The crude product is reacted further to give Example 3A without purification.

Example 3A

2-Chloro-4-trifluoromethoxybenzonitrile

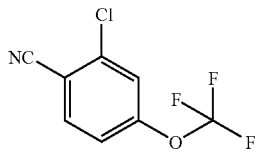

3.00 g of the compound from Example 2A are dissolved in 12 ml of degassed DMF with 2.04 g of zinc cyanide and 1.00 g of tetrakis(triphenylphosphine)palladium and the mixture is heated under argon at 120° C. for 2 h. After cooling, the reaction mixture is diluted with ethyl acetate and extracted by shaking twice with a saturated sodium hydrogen carbonate solution and then with a saturated sodium chloride solution. The organic phase is dried over sodium sulfate and concentrated. The residue is purified by silica gel chromatography (cyclohexane/ethyl acetate 10:1).

$^1$H NMR (300 MHz, DMSO-$d_6$): δ=7.62 (dd, 1H), 7.95 (d, 1H), 8.18 (d, 1H).

Example 4A

2-Methyl-4-(trifluoromethoxy)benzamide

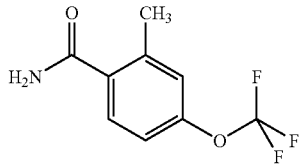

795 mg (3.61 mmol) of 2-methyl-4-(trifluoromethoxy) benzoic acid are heated under reflux with 4 ml (54.8 mmol) of thionyl chloride and one drop of DMF for 30 minutes. After cooling, the reaction solution is slowly added dropwise into an ice-cooled concentrated aqueous ammonia solution. The resulting precipitate is collected by suction filtration, taken up in 30 ml of water and stirred at 60° C. for 1 h. The mixture is allowed to cool and the solid is collected by filtration and dried in vacuo. Yield: 562 mg (71% of theory).

LC-MS (method 2): $R_t$=1.61 min.

MS (ESI$^+$): m/z=220 (M+H)$^+$

1H NMR (400 MHz, DMSO-$d_6$): δ=7.79 (bs, 1H), 7.42-7.50 (m, 2H), 7.19-7.28 (m, 2H), 2.39 (s, 3H).

Example 5A

2-Methyl-4-(trifluoromethoxy)benzylamine

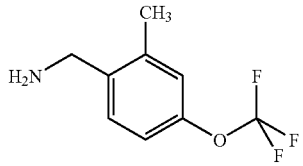

18.8 ml (18.8 mmol) of borane-THF complex (1M) are provided under argon with ice cooling. A solution of 823 mg (3.76 mmol) of 2-methyl-4-(trifluoromethoxy)benzamide (Example 4A) in 80 ml of THF is added dropwise and the mixture is subsequently stirred under reflux for 8 h. With ice cooling, 80 ml of 1N hydrochloric acid are added dropwise (until the evolution of gas comes to an end) and the mixture is heated under reflux for 1 h. The reaction mixture is subsequently rendered alkaline using a 1N sodium hydroxide solution and extracted three times with dichloromethane, the combined organic phases are dried over sodium sulfate and the solvent is removed in vacuo. An oil is obtained which is reacted further without further purification.

Yield: 732 mg (95% of theory).

LC-MS (method 3): $R_t$=1.41 min.

MS (ESI$^+$): m/z=206 (M+H)$^+$ $^1$H NMR (400 MHz, CDCl$_3$): δ=7.32-7.40 (m, 1H), 6.99-7.11 (m, 2H), 3.95-4.01 (m, 2H), 2.40 (s, 3H).

Example 6A

2-Bromo-4-chlorobenzylamine

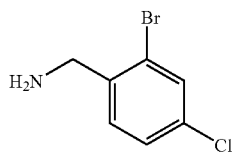

13.9 ml of borane-THF complex are provided with ice cooling. Slowly a solution of 2.0 g of 2-bromo-4-chlorobenzonitrile (Example 1A) in 60 ml of THF is added. Thereafter the reaction mixture is heated under reflux for 1 h, cooled, and 20 ml of 1N hydrochloric acid are added dropwise, with ice cooling. The mixture is heated under reflux for 1 h and allowed to cool. For the work-up, the solution is rendered alkaline using a 1N sodium hydroxide solution and extracted with dichloromethane. The organic phase is dried over sodium sulfate and concentrated on a rotary evaporator. The crude product is reacted further without purification.

$^1$H NMR (300 MHz, CDCl$_3$): δ=3.89 (s, 2H), 7.35-7.45 (m [ABM], 2H), 7.55 (d, 1H).

Example 7A

2-Chloro-4-trifluoromethoxybenzylamine hydrochloride

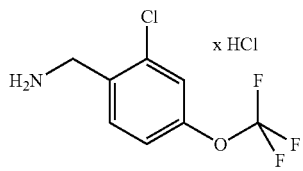

The preparation takes place in analogy to Example 6A from the compound from Example 3A with subsequent treatment with 4N hydrochloric acid in dioxane.

¹H NMR (300 MHz, DMSO-d₆): δ=4.15 (s, 2H), 7.52 (d, 1H), 7.70 (s, 1H), 7.78 (d, 1H), 8.56 (bs, 3H).

Example 8A 2,4-Dichloro-6-methylbenzylamine hydrochloride

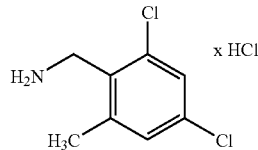

The preparation takes place in analogy to Example 6A from 2,4-dichloro-6-methylbenzonitrile with subsequent treatment with 4N hydrochloric acid in dioxane.
¹H NMR (300 MHz, DMSO-d₆): δ=2.5 (s, 3H), 4.10 (s, 2H), 7.40 (s, 1H), 7.60 (s, 1H), 8.40 (bs, 3H).
LC-MS (method 13): $R_t$=2.44 min, MS (ES+)=190 (M+H)⁺.

Example 9A

4-Chloro-2-trifluoromethylbenzylamine hydrochloride

The preparation takes place in analogy to Example 6A from 4-chloro-2-trifluoro-methylbenzonitrile with subsequent treatment with 4N hydrochloric acid in dioxane.
¹H NMR (300 MHz, DMSO-d₆): δ=4.18 (d, 2H), 7.82 (d, 1H), 7.88-7.98 (m, 2H), 8.58 (bs, 3H).

Example 10A

Ethyl 3-[(2,2,2-trifluoroethyl)amino]-2-(2,4,5-trifluoro-3-methoxybenzoyl)acrylate (E+Z)

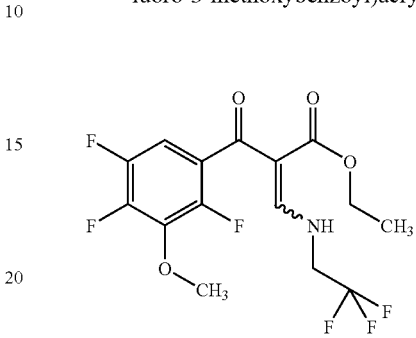

2.00 g (5.79 mmol) of ethyl 3-oxo-3-(2,4,5-trifluoro-3-methoxyphenyl)propanoate (for preparation see Journal of Medicinal Chemistry (1995), 38 (22), 4478-87) are stirred under reflux in 3.8 ml (4.14 g, 40.55 mmol) of acetic anhydride and 4.82 ml (4.29 g, 28.96 mmol) of triethyl orthoformate for 2 h. The solvent is subsequently removed completely on a rotary evaporator and the residue is dissolved in 10 ml of ethanol. 1.03 g (10.43 mmol) of 2,2,2-trifluoro-1-aminoethane are added dropwise to the ice-cooled solution, and the mixture is brought to room temperature and stirred at that temperature overnight. For the work-up, the solvent is removed and the residue is reacted further as a crude product without purification steps.
LC-MS (method 2): $R_t$=2.37 min, MS (ES+)=386 (M+H)⁺.

The following Examples 11A to 14A are prepared in analogy to Example 10A from the corresponding amines.

| Example No. | Structure | Analytical data LC-MS (method)/measurement values |
|---|---|---|
| 11A (S-enantiomer) | 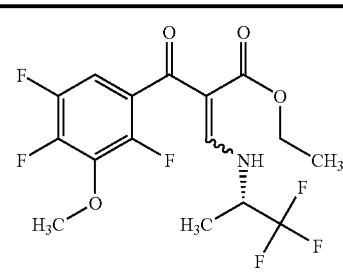 | LC-MS (method 1): $R_t$ = 2.47 min MS (ES+): m/z = 400 (M + H)⁺ |
| 12A | 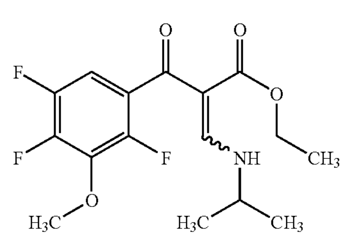 | LC-MS (method 1): $R_t$ = 2.56 min MS (ES+): m/z = 346 (M + H)⁺ |

| Example No. | Structure | Analytical data LC-MS (method)/measurement values |
|---|---|---|
| 13A | 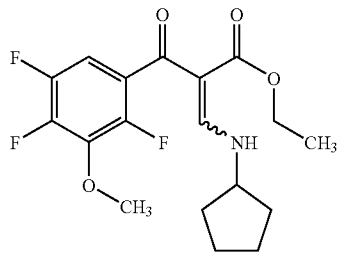 | LC-MS (method 1):<br>$R_t$ = 2.77 min<br>MS (ES+):<br>m/z = 372 (M + H)+ |
| 14A<br>(1S,2R)-<br>enantiomer | | LC-MS (method 1):<br>$R_t$ = 2.40 min<br>MS (ES+):<br>m/z = 382 (M + H)+ |

Example 15A

Ethyl 6,7-difluoro-8-methoxy-4-oxo-1-(2,2,2-trifluoroethyl)-1,4-dihydroquinoline-3-carboxylate

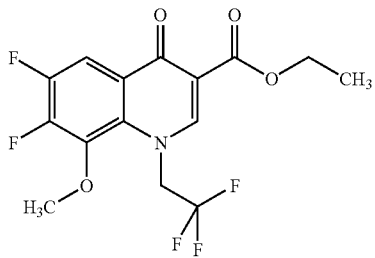

Under an argon atmosphere and with ice cooling 0.32 g (8.11 mmol) of 60% sodium hydride are provided in 5 ml of tetrahydrofuran, and a solution of 2.23 g (5.79 mmol) of the compound from Example 10A in 15 ml of tetrahydrofuran is slowly added dropwise. The mixture is subsequently warmed to room temperature, stirred at that temperature for 2 h and left to stand overnight. For the work-up, 2 ml of acetic acid are added dropwise, the mixture is stirred for 5 min, diluted with ethyl acetate, washed several times with water and once with a saturated sodium hydrogen carbonate solution, the organic phase is dried over magnesium sulfate and filtered, and the solvent is removed completely on a rotary evaporator. The crude product is prepurified by column chromatography on silica gel 60 (eluent: dichloromethane/methanol 100/1→100/2) and after fine purification via preparative RP-HPLC (method 5) 1.8 g of product are obtained.

HPLC (method 10): $R_t$=4.34 min,
MS (DCI (NH$_3$))=366 (M+H)+.
$^1$H NMR (300 MHz, CDCl$_3$): δ=1.41 (t, 3H), 4.15 (s, 3H), 4.41 (q, 2H), 5.23 (q, 2H), 8.11 (dd, 1H), 8.33 (s, 1H).

Examples 16A to 19A listed in the following table are prepared in analogy to Example 15A.

| Example No. | Structure | Starting material Example No. | Analytical data LC-MS (method)/measurement values |
|---|---|---|---|
| 16A<br>(S)-enantiomer | | 11A | LC-MS (method 1):<br>$R_t$ = 2.22 min<br>MS (ES+):<br>m/z = 380 (M + H)+ |

| Example No. | Structure | Starting material Example No. | Analytical data LC-MS (method)/measurement values |
|---|---|---|---|
| 17A | 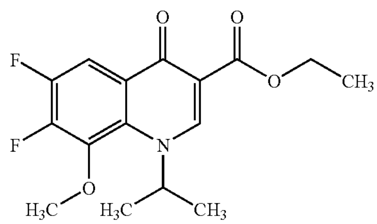 | 12A | LC-MS (method 1):<br>$R_t$ = 2.16 min<br>MS (ES+):<br>m/z = 326 (M + H)$^+$ |
| 18A | 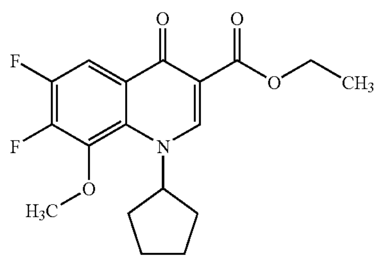 | 13A | LC-MS (method 3):<br>$R_t$ = 2.46 min<br>MS (ES+):<br>m/z = 352 (M + H)$^+$ |
| 19A<br>(1S,2R)-<br>enantiomer | | 14A | LC-MS (method 2):<br>$R_t$ = 1.76 min<br>MS (ES+):<br>m/z = 342 (M + H)$^+$ |

Example 20A

6,7-Difluoro-8-methoxy-4-oxo-1-(2,2,2-trifluoroethyl)-1,4-dihydroquinoline-3-carboxylic acid

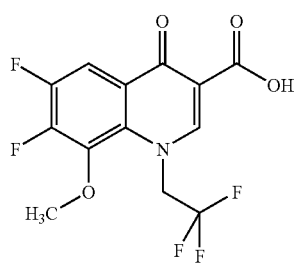

800 mg (2.19 mmol) of the compound from Example 15A are provided in a mixture of 25 ml of acetic acid-water-sulfuric acid 12:8:1 and stirred under reflux overnight. For the work-up, the solvent is largely removed on a rotary evaporator, the residue is cautiously adjusted to pH 3, using a saturated sodium hydrogen carbonate solution, with ice cooling, the suspension is diluted with water and the precipitate is collected by suction filtration and, after drying of the filter residue under high vacuum, 575 mg of the title compound are obtained.

LC-MS (method 3): $R_t$=2.41 min, MS (ES+)=338 (M+H)$^+$.

$^1$H NMR (300 MHz, CDCl$_3$): δ=4.21 (s, 3H), 5.37 (q, 2H), 8.11 (dd, 1H), 8.62 (s, 1H), 14.05 (bs, 1H).

The following Examples 21A to 24A are prepared in analogy to Example 20A.

| Example No. | Structure | Starting material | Analytical data LC-MS (method)/measurement values HPLC (method)/measurement value MS (method)/measurement value |
|---|---|---|---|
| 21A (S)-enantiomer | 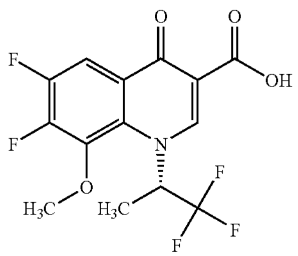 | 16A | HPLC (method 10): $R_t$ = 4.54 min MS (ESI+): m/z = 374 (M + Na)$^+$ |
| 22A | 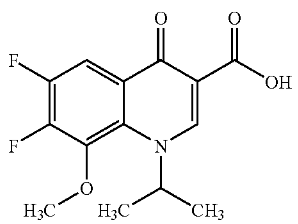 | 17A | LC-MS (method 3): $R_t$ = 2.27 min MS (ES+): m/z = 298 (M + H)$^+$ |
| 23A | 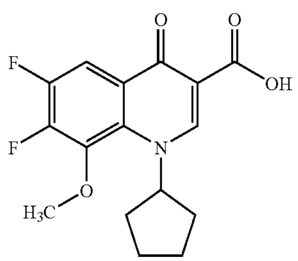 | 18A | LC-MS (method 1): $R_t$ = 2.40 min MS (ES+): m/z = 324 (M + H)$^+$ |
| 24A (1S,2R)-enantiomer | 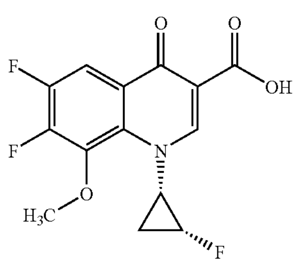 | 19A | LC-MS (method 2): $R_t$ = 1.84 min MS (ES+): m/z = 313 (M + H)$^+$ |

Example 25A

[6,7-Difluoro-8-methoxy-4-oxo-1-(2,2,2-trifluoroethyl)-1,4-dihydroquinolin-3-yl]carbonyl difluoroborate

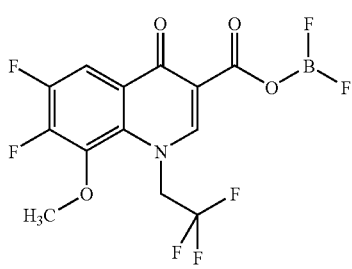

1.5 g (4.30 mmol) of the compound from Example 20A are provided in 10 ml of tetrahydrofuran, subsequently 6.81 ml (7.63 g, 53.75 mmol) of boron trifluoridediethyl ether complex are added and the mixture is stirred overnight at 70° C. For the work-up, 50 ml of diethyl ether are added to the reaction mixture, cooled to room temperature, the mixture is stirred for 20 min and the precipitate formed is collected by suction filtration. After drying the residue under high vacuum, 1150 mg of the title compound are obtained and reacted further without purification.

HPLC (method 9): $R_t$=4.25 min,

MS (DCI (NH$_3$))=402 (M+NH)$^+$.

$^1$H NMR (300 MHz, DMSO-d$_6$): δ=4.21 (s, 3H), 6.12 (q, 2H), 8.38 (dd, 1H), 9.66 (s, 1H).

The following Examples 26A to 29A are prepared in analogy to Example 25A.

| Example No. | Structure | Starting material | Analytical data LC-MS (method)/measurement values |
|---|---|---|---|
| 26A (S)-enantiomer | 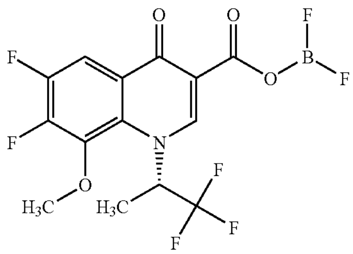 | 21A | LC-MS (method 2): $R_t = 1.98$ min MS (ES+): m/z = 400 (M + H)$^+$ |
| 27A | 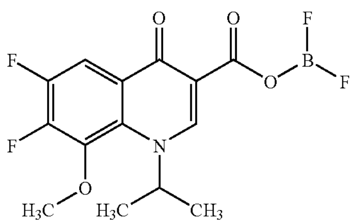 | 22A | LC-MS (method 3): $R_t = 1.83$ min MS (ES+): m/z = 346 (M + H)$^+$ |
| 28A | 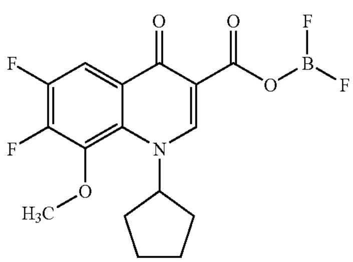 | 23A | LC-MS (method 2): $R_t = 2.02$ min MS (ES+): m/z = 372 (M + H)$^+$ |
| 29A (1S,2R)-enantiomer | 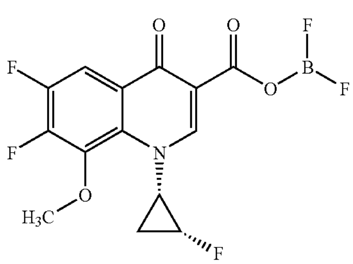 | 24A | LC-MS (method 2): $R_t = 1.74$ min MS (ES+): m/z = 361 (M + H)$^+$ |

Example 30A

[1-Cyclopropyl-7-fluoro-8-trifluoromethyl-4-oxo-1,4-dihydroquinolin-3-yl]carbonyl difluoroborate

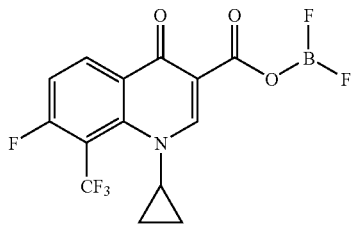

The compound is prepared in analogy to Example 25A from 1-cyclopropyl-7-fluoro-8-trifluoromethyl-4-oxo-1,4-dihydroquinolin-3-yl]carboxylic acid (for preparation: see DE 4301246).

LC-MS (method 1): $R_t$=2.13 min+

MS (ES+): m/z=364 (M+H)$^+$

Example 31A

7-[(3RS,5SR)-3,5-Dimethylpiperazin-1-yl]-6-fluoro-8-methoxy-4-oxo-1-(2,2,2-trifluoroethyl)-1,4-dihydroquinoline-3-carboxylic acid hydroformate

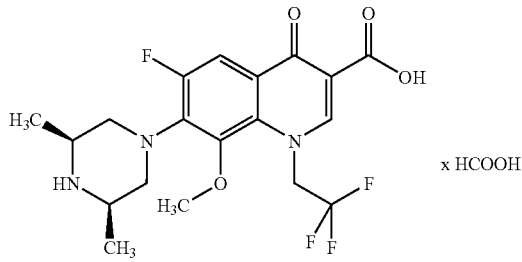

300.0 mg (0.78 mmol) of the compound from Example 25A and 213.6 mg (1.87 mmol) of cis-2,6-dimethylpiperazine are stirred in 6 ml of acetonitrile at 50° C. overnight. The solvent is removed completely on a rotary evaporator, and the residue is stirred under reflux with a mixture of 12 ml of ethanol and 6 ml of triethylamine for 1 h. For the work-up, the solvent is removed on a rotary evaporator. After fine purification via preparative RP-HPLC (method 5) 260 mg of the target compound are obtained.

HPLC (method 9): $R_t$=3.76 min,
MS (ESI+)=432 (M+H)$^+$.
$^1$H NMR (300 MHz, DMSO-d$_6$): δ=1.03 (d, 6H), 2.82 (m, 2H), 3.04 (m, 2H), 3.28 (m, 2H), 3.78 (s, 3H), 5.77 (q, 2H), 7.82 (d, 1H), 8.19 (s, 1H), 8.52 (s, 1H).

The following Examples 32A to 36A are prepared in analogy to Example 31A.

| Example No. | Structure | Starting material | Analytical data LC-MS (method)/measurement values HPLC (method)/measurement value MS (method)/measurement value |
|---|---|---|---|
| 32A (S)-enantiomer | | 26A | HPLC (method 10): $R_t$ = 3.76 min MS (ESI+): m/z = 446 (M + H)$^+$ |
| 33A | 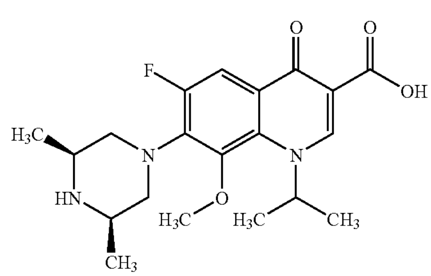 | 27A | HPLC (method 9): $R_t$ = 3.54 min MS (ESI+): m/z = 392 (M + H)$^+$ |

| Example No. | Structure | Starting material | Analytical data LC-MS (method)/measurement values HPLC (method)/measurement value MS (method)/measurement value |
|---|---|---|---|
| 34A | 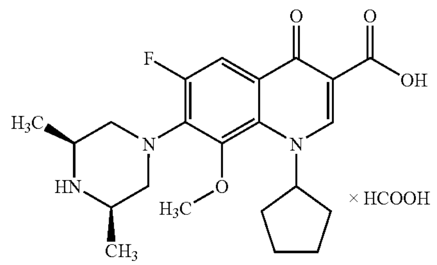 | 28A | HPLC (method 9): $R_t$ = 3.84 min MS (DCI (NH$_3$)): m/z = 418 (M + H)$^+$ |
| 35A (1S,2R)-enantiomer | | 29A | LC-MS (method 2): $R_t$ = 1.02 min MS (ES+): m/z = 407 (M + H)$^+$ |
| 36A | 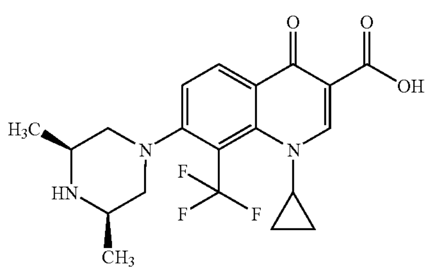 | 30A | LC-MS (method 2): $R_t$ = 1.08 min MS (ES+): m/z = 410 (M + H)$^+$ |

Example 37A

N-(2,4-Dichlorobenzyl)-7-[(3RS,5RS)-3,5-dimethylpiperazin-1-yl]-6-fluoro-8-methoxy-1-(2,2,2-trifluoroethyl)-4-oxo-1,4-dihydroquinoline-3-carboxamide

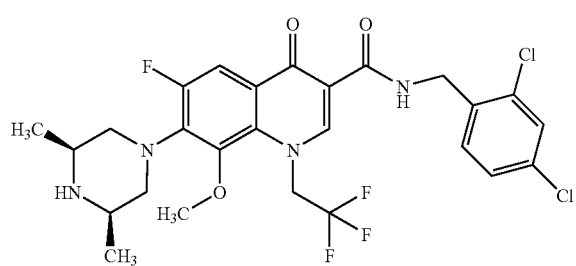

Under argon, 7.52 g (58.2 mmol) of N,N-diisopropylethylamine and 7.71 g (14.81 mmol) of PyBOP are added to 5.20 g (10.58 mmol) of 7-(cis-3,5-dimethylpiperazin-1-yl)-6-fluoro-8-methoxy-1-(2,2,2-trifluoroethyl)-4-oxo-1,4-dihydroquinoline-3-carboxylic acid hydroformate (Example 31A) and 3.73 g (21.2 mmol) of 2,4-dichlorobenzylamine in 10.7 ml of dimethylformamide and the mixture is stirred at room temperature overnight. The reaction mixture is diluted with 1500 ml of ethyl acetate and washed three times with water. The combined aqueous phases are extracted once with ethyl acetate. The combined organic phases are washed with a saturated sodium chloride solution, dried over sodium sulfate and concentrated. The residue is stirred with 30 ml of acetonitrile. The solid is then collected by filtration and dried under high vacuum. 6.80 mg of the target compound are obtained as a cocrystallisate with 1 eq. of acetonitrile. For smaller quantities the residue after extraction can be purified by preparative HPLC (by one of the methods 5 to 8).

HPLC (method 9): $R_t$=4.59 min.

MS (ESI)=589 (M+H)$^+$.

$^1$H NMR (300 MHz, CDCl$_3$): δ=1.11 (d, 6H), 2.01 (3H, CH$_3$CN), 2.82 (br.t, 2H), 3.03-3.16 (m, 2H), 3.29 (br.d, 2H), 3.79 (s, 3H), 4.69 (d, 2H), 5.25 (q, 2H), 7.20 (dd, 1H), 7.37-7.42 (m, 2H), 7.91 (d, 1H), 8.54 (s, 1H), 10.24 (t, 1H).

Example 38A

N-(2,4-Dichlorobenzyl)-7-[(3RS,5RS)-3,5-dimethylpiperazin-1-yl]-6-fluoro-8-methoxy-1-(2,2,2-trifluoroethyl)-4-oxo-1,4-dihydroquinoline-3-carboxamide hydrochloride

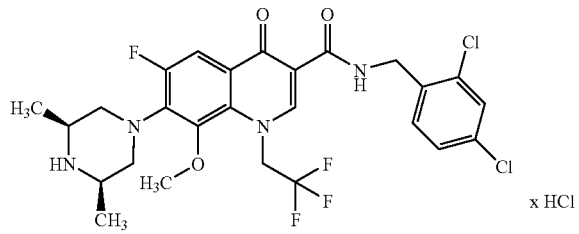

6780 mg of the compound from Example 37A (contains 1 eq. of acetonitrile) are dissolved in 4.3 ml of 4N hydrogen chloride in dioxane, the solution is concentrated on a rotary evaporator and the residue is then dried under high vacuum. Yield: 6730 mg (quantitative).

HPLC (method 9): $R_t$=4.57 min

MS (ESI): m/z=589 (M+H)$^+$ $^1$H NMR (400 MHz, DMSO-d$_6$): δ=1.38 (d, 6H), 3.222 (br.t, 2H), 3.38-3.52 (m, 4H), 3.83 (s, 3H), 4.60 (d, 2H), 5.71 (q, 2H), 7.39-7.46 (m, 2H), 7.65 (s, 1H), 7.84 (d, 1H), 8.76 (br.s, 1H), 8.89 (s, 1H), 9.35 (br.s, 1H), 10.10 (t, 1H).

Example 39A

1-Cyclopropyl-N-(2,4-dichlorobenzyl)-7-[(3RS,5SR)-3,5-dimethylpiperazin-1-yl]-6-fluoro-8-methoxy-4-oxo-1,4-dihydroquinoline-3-carboxamide

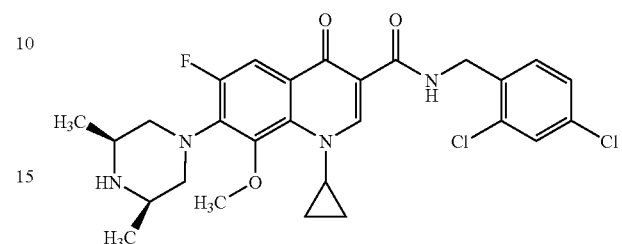

The preparation takes place in analogy to Example 37A, from 1-cyclopropyl-7-(cis-3,5-dimethylpiperazin-1-yl)-6-fluoro-8-methoxy-4-oxo-1,4-dihydroquinoline-3-carboxylic acid (for preparation see: Journal of Medicinal Chemistry, (1995), 38(22), 4478-87).

LC-MS (method 2): $R_t$=1.77 min,

MS (ES+)=547 (M+H)$^+$

Examples 40A to 44A are prepared from the same acid as in Example 39A and in analogy to the preparation instructions of Example 37A.

| Example No. | Structure | Amine starting material Ex. No. | Analytical data LC-MS (method)/measurement values |
|---|---|---|---|
| 40A | 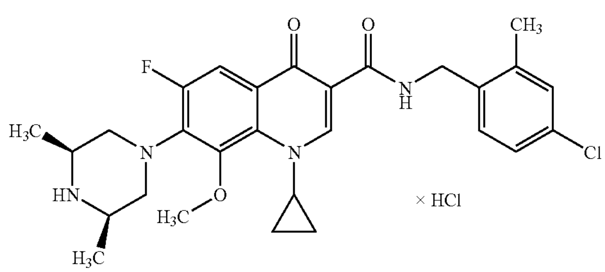 | 4-chloro-2-methyl-benzyl-amine | LC-MS (method 3): $R_t$ = 1.85 min MS (ES+): m/z = 527 (M + H)$^+$ |
| 41A | 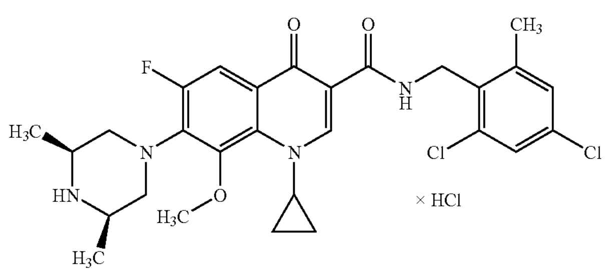 | 8A | LC-MS (method 3): $R_t$ = 1.91 min MS (ES+): m/z = 561 (M + H)$^+$ |

-continued

| Example No. | Structure | Amine starting material Ex. No. | Analytical data LC-MS (method)/measurement values |
|---|---|---|---|
| 42A | (structure shown) × HCl | 9A | LC-MS (method 3): $R_t$ = 1.91 min MS (ES+): m/z = 581 (M + H)$^+$ |
| 43A | (structure shown) × HCOOH | 7A | LC-MS (method 2): $R_t$ = 1.86 min MS (ES+): m/z = 597 (M + H)$^+$ |
| 44A | (structure shown) × HCOOH | 6A | LC-MS (method 2): $R_t$ = 1.74 min MS (ES+): m/z = 591 (M + H)$^+$ |

Example 45A

8-Chloro-1-cyclopropyl-N-(2,4-dichlorobenzyl)-7-[(3RS,5SR)-3,5-dimethylpiperazin-1-yl]-6-fluoro-4-oxo-1,4-dihydroquinoline-3-carboxamide

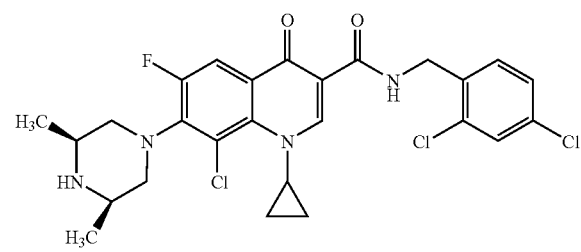

The preparation takes place in analogy to Example 37A, from 8-chloro-1-cyclopropyl-7-[(3RS,5SR)-3,5-dimethylpiperazin-1-yl]-6-fluoro-4-oxo-1,4-dihydroquinoline-3-carboxylic acid (for preparation see: DE 3635218) using hydroxybenzotriazole and EDC instead of PyBOP.

LC-MS (method 2): $R_t$=1.86 min,

MS (ES+)=551 (M+H)$^+$ $^1$H NMR (400 MHz, CDCl$_3$): δ=0.9 (m, 2H), 1.1 (d, 6H), 1.2-1.3 (m, 2H), 2.7-2.9 (m, 2H), 3.1-3.3 (m, 4H), 4.3 (m, 1H), 4.7 (d, 2H), 7.2 (dd, 2H), 7.4 (m, 2H), 8.0 (d, 1H), 8.9 (s, 1H), 10.2 (t, 1H).

Examples 46A and 47A are prepared from the same acid as in Example 45A and in analogy to the preparation instructions of Example 37A.

| Example No. | Structure | Amine starting material Ex. No. | Analytical data LC-MS (method)/measurement values |
|---|---|---|---|
| 46A | 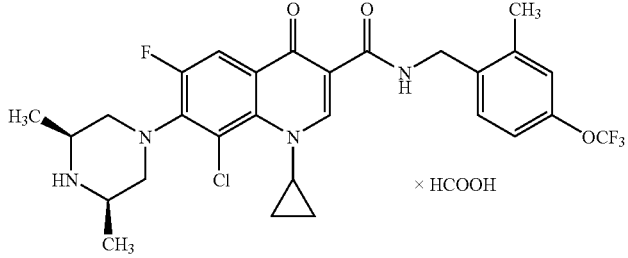 | 5A | LC-MS (method 1): $R_t$ = 1.91 min MS (ES+): m/z = 581 (M + H)$^+$ |
| 47A | 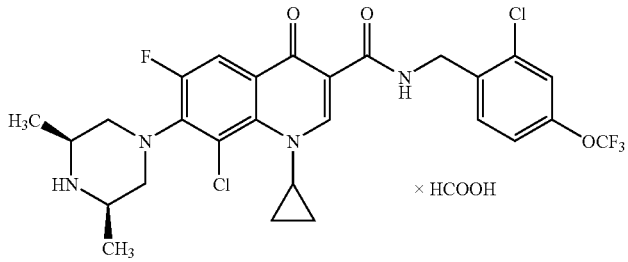 | 7A | LC-MS (method 3): $R_t$ = 2.02 min MS (ES+): m/z = 601 (M + H)$^+$ |

Examples 48A to 50A are prepared from 1-cyclopropyl-6-fluoro-8-methoxy-7-(3-methylpiperazin-1-yl)-4-oxo-1,4-dihydroquinoline-3-carboxylic acid (for preparation: see Journal of Medicinal Chemistry 1995, 38(22) 4478) and in analogy to the preparation instructions of Example 37A.

| Example No. | Structure | Amine starting material Ex. No. | Analytical data LC-MS (method)/measurement values |
|---|---|---|---|
| 48A | 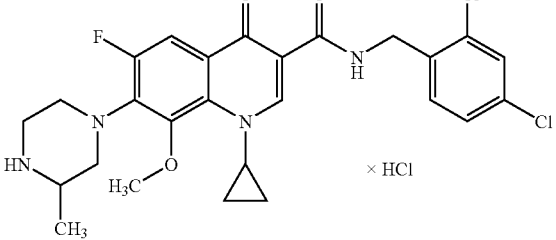 | Dichlorobenzylamine | LC-MS (method 2): $R_t$ = 2.05 min MS (ES+): m/z = 542 (M + H)$^+$ |
| 49A | 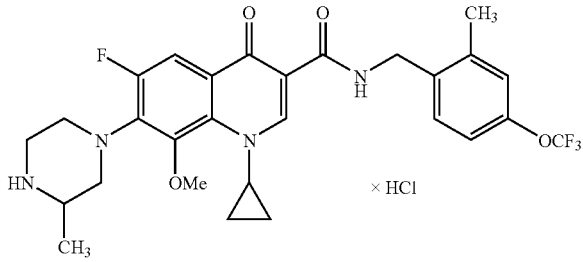 | 5A | LC-MS (method 1): $R_t$ = 1.86 min MS (ES+): m/z = 563 (M + H)$^+$ |

-continued

| Example No. | Structure | Amine starting material Ex. No. | Analytical data LC-MS (method)/measurement values |
|---|---|---|---|
| 50A | 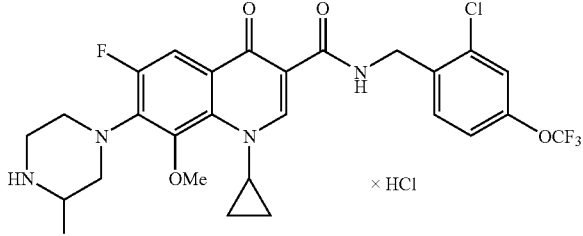 | 7A | LC-MS (method 3):<br>$R_t$ = 1.98 min<br>MS (ES+):<br>m/z = 583 (M + H)$^+$ |

Example 51A

N-(4-Bromo-2-chlorobenzyl)-7-[(3RS,5RS)-3,5-dimethylpiperazin-1-yl]-6-fluoro-1-(2-fluoroethyl)-8-methoxy-4-oxo-1,4-dihydroquinoline-3-carboxamide hydroformate

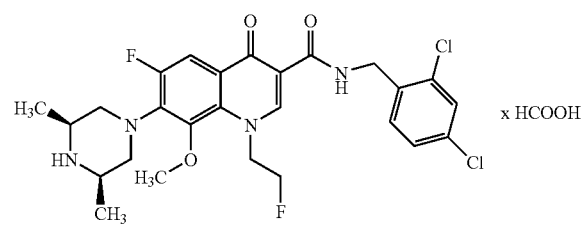

The preparation takes place in analogy to Example 37A, from 7-(cis-3,5-dimethylpiperazin-1-yl)-6-fluoro-1-(2-fluoroethyl)-8-methoxy-4-oxo-1,4-dihydroquinoline-3-carboxylic acid (for preparation see: EP 0241206) and 2,4-dichlorobenzylamine.

HPLC (method 9): $R_t$=4.46 min, MS (ESI)=553 (M+H)$^+$.

$^1$H NMR (400 MHz, DMSO-d$_6$): δ=1.15 (d, 6H), 2.88-3.07 (m, 2H), 3.11-3.56 (m, 4H underneath the water signal of the DMSO), 3.78 (s, 3H), 4.59 (d, 2H), 4.76 (dd, 2H), 4.95 (d, 2H), 7.35-7.50 (m, 2H), 7.64 (s, 1H), 7.83 (d, 1H), 8.16 (s, 1H), 8.72 (s, 1H), 10.27 (t, 1H).

Examples 52A to 57A are prepared in analogy to the preparation instructions of Example 37A, from various carboxylic acids and benzylamines.

| Example No. | Structure | Starting materials Ex. No. | Analytical data LC-MS (method)/measurement values HPLC (method)/measurement value MS (method)/measurement value NMR spectrum |
|---|---|---|---|
| 52A (1S,2R)-enantiomer | 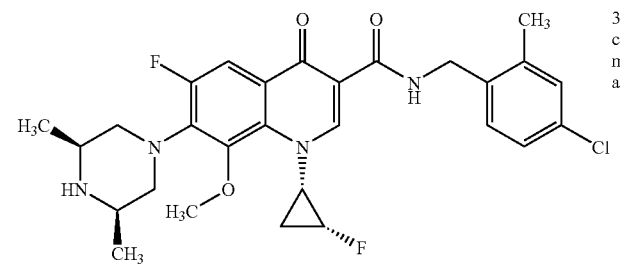 | 35A and 4-chloro-2-methylbenzylamine | LC-MS (method 3):<br>$R_t$ = 1.97 min<br>MS (ES+):<br>m/z = 545 (M + H)$^+$<br>$^1$H NMR (400 MHz, DMSO-d$_6$): δ = 1.06 (d, 6 H), 1.43-1.68 (m, 2 H), 2.32 (s, 3 H), 2.72-2.91 (m, 2 H), 3.06 (m, 2 H), 3.25 (m, 2 H), 3.77 (s, 3 H), 4.08 (m, 1 H), 4.51 (d, 2 H), 4.93/5.10 (2 m, 1 H), 7.19-7.32 (m, 3 H), 7.71 (d, 1 H), 8.68 (s, 1 H), 10.08 (t, 1 H) |
| 53A (S)-enantiomer | 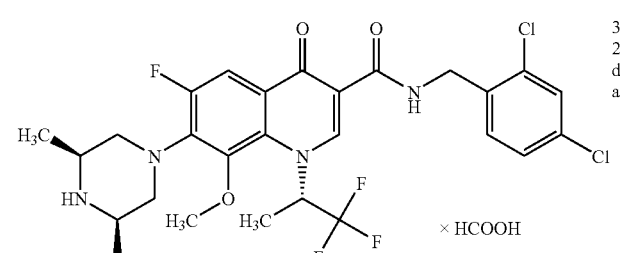 | 32A and 2,4-dichlorobenzylamine | HPLC (method 9):<br>$R_t$ = 4.75 min<br>MS (ESI)<br>m/z = 603 (M + H)$^+$ |

-continued

| Example No. | Structure | Starting materials Ex. No. | Analytical data LC-MS (method)/measurement values HPLC (method)/measurement value MS (method)/measurement value NMR spectrum |
|---|---|---|---|
| 54A | 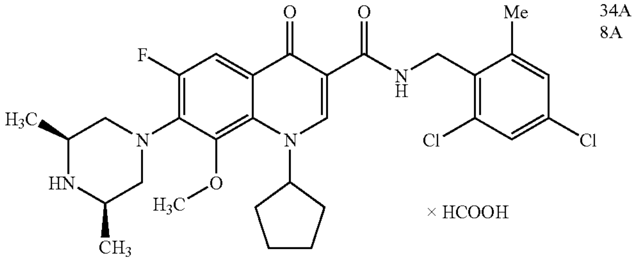 | 34A and 8A | LC-MS (method 3): $R_t$ = 2.18 min MS (ES+): m/z = 589 (M + H)$^+$ |
| 55A | 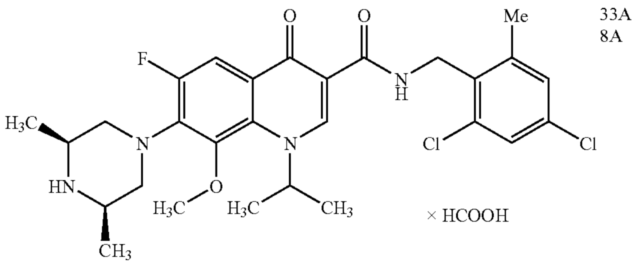 | 33A and 8A | LC-MS (method 2): $R_t$ = 1.72 min MS (ES+): m/z = 563 (M + H)$^+$ |
| 56A | 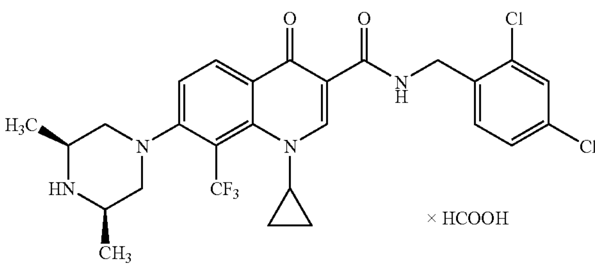 | 36A and 2,4-dichloro-benzylamine | LC-MS (method 3): $R_t$ = 2.13 min MS (ES+): m/z = 567 (M + H)$^+$ |
| 57A (1S,2R)-enantio-mer | 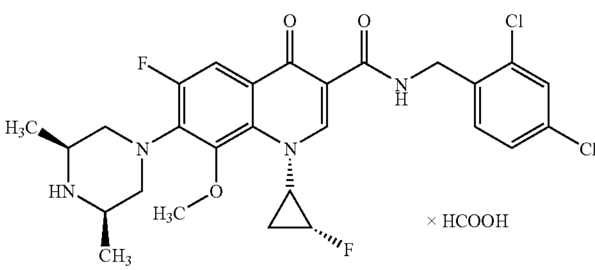 | 35A and 2,4-dichloro-benzylamine | LC-MS (method 1): $R_t$ = 1.97 min MS (ES+): m/z = 565 (M + H)$^+$ |

Example 58A (3S)-N-(2,4-Dichlorobenzyl)-9,10-difluoro-3-methyl-7-oxo-2,3-dihydro-7H-[1,4]oxazino[2,3,4-ij]quinoline-6-carboxamide

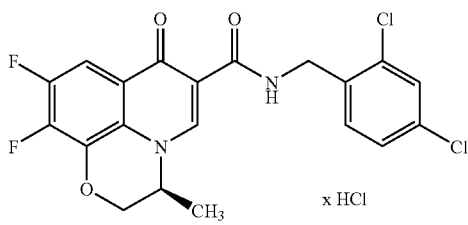

The compound is prepared in analogy to the instructions of Example 37A, from (3S)-9,10-difluoro-3-methyl-7-oxo-2,3-dihydro-7H-[1,4]oxazino[2,3,4-ij]quinoline-6-carboxylic acid (for preparation: see Journal of Medicinal Chemistry 1987, 30(12), 2283-2286) and 2,4-dichlorobenzylamine.

LC-MS (method 1): $R_t$=2.59 min

MS (ES+): m/z=439 (M+H)$^+$.

$^1$H NMR (300 MHz, CDCl$_3$): δ=1.62 (d, 3H), 4.38-4.54 (m, 3H), 4.71 (dd, 2H), 7.11 (dd, 1H), 7.49 (d, 1H), 7.50 (d, 1H), 7.86 (dd, 1H), 8.71 (1H), 10.47 (t, 1H).

Example 59A (3S)-N-(2,4-Dichlorobenzyl)-10-{(3RS,5SR)-3,5-dimethylpiperazin-1-yl}-9-fluoro-3-methyl-7-oxo-2,3-dihydro-7H-[1,4]oxazino[2,3,4-ij]quinoline-6-carboxamide hydrochloride

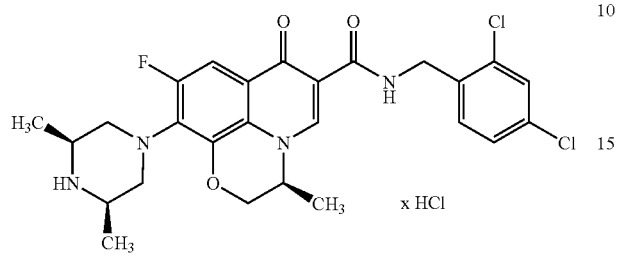

100 mg of the compound from Example 58A are heated at 100° C. overnight in 2 ml of DMSO with 39 mg of cis-dimethylpiperazine and 69 mg of triethylamine, and subsequently at 150° C. for a further 15 minutes. After cooling, the reaction mixture is separated directly by preparative HPLC (method 6). 54 mg (41% of theory) of the title compound are obtained.

LC-MS (method 2): $R_t$=1.66 min
MS (ES+): m/z=533 (M+H)$^+$.

Example 60A tert-Butyl (3RS,5SR)-4-(2-ethoxy-2-oxoethyl)-3,5-dimethylpiperazine-1-carboxylate

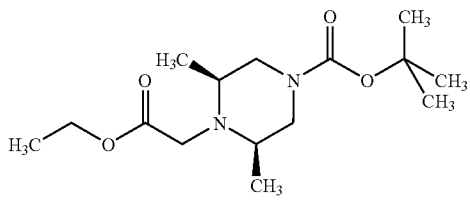

2.0 g (9.33 mmol) of tert-butyl (3RS,5SR)-3,5-dimethylpiperazine-1-carboxylate (preparation: Helvetica Chimica Acta 1990, 73 (4), 839-855), 2.3 g (18.67 mmol) of ethyl chloroacetate, 3.9 g (28.00 mmol) of potassium carbonate and 0.5 g (2.80 mmol) of potassium iodide are stirred under reflux overnight in 80 ml of acetonitrile. For the work-up, some of the acetonitrile is removed on a rotary evaporator, and the residue is diluted with ethyl acetate, subsequently washed twice with water and once with a saturated sodium chloride solution. The combined aqueous phases are extracted once with ethyl acetate, the combined organic phases are dried over sodium sulfate, and the solvent is removed completely on a rotary evaporator. The residue is taken up in cyclohexane and after subsequent elution over silica gel 60 using subatmospheric pressure (cyclohexane/ethyl acetate 100/10→80/10→40/10) 2.5 g (88% of theory) of product are obtained.

MS (ESI+): m/z=301 (M+H)$^+$
$^1$H NMR (300 MHz, CDCl$_3$): δ=1.08 (d, 6H), 1.28 (t, 3H), 1.45 (s, 9H), 2.53 (m, 2H), 2.89 (m, 2H), 3.57 (s, 2H), 3.70-4.06 (m, 2H), 4.17 (q, 2H).

Example 61A tert-Butyl (3RS,5SR)-4-(2-ethoxy-1-methyl-2-oxoethyl)-3,5-dimethylpiperazine-1-carboxylate

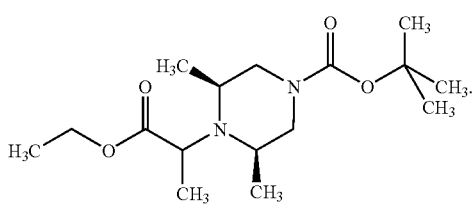

0.5 ml (377.2 mg, 3.73 mmol) of diisopropylamine are provided in 2 ml of tetrahydrofuran at −10° C., 2.3 ml (238.8 mg, 3.73 mmol) of a 1.6 M n-butyllithium solution in tetrahydrofuran are added slowly, and, after the addition has been completed, the mixture is stirred at 5° C. for 10 minutes. 400.0 mg (1.33 mmol) of the compound from Example 60A are provided in a mixture of 4 ml of tetrahydrofuran and 1 ml of hexamethylphosphoric triamide at −78° C., half of the freshly prepared lithium diisopropylamide solution is added slowly, the mixture is stirred at −78° C. for 45 minutes, and the reaction is warmed to −15° C., and stirred at this temperature for 15 minutes. The mixture is again cooled to −78° C., subsequently 0.1 ml (245.7 mg, 1.73 mmol) of iodomethane dissolved in 1 ml of tetrahydrofuran is added dropwise and the reaction is warmed to room temperature overnight with stirring. The mixture is again cooled to −78° C., the remaining lithium diisopropylamide solution is added, the mixture is stirred at −78° C. for 45 minutes and at −15° C. for 20 minutes, then 0.1 ml (245.7 mg, 1.73 mmol) of iodomethane are again added dropwise at −78° C., and the mixture is brought slowly to room temperature overnight with stirring. For the work-up, the reaction is quenched using a 10% ammonium chloride solution, and the mixture is diluted with ethyl acetate, subsequently washed in succession once with a saturated sodium hydrogen carbonate solution, twice with water, and once with a saturated sodium chloride solution, and the organic phase is dried over sodium sulfate and filtered, and the solvent is removed completely on a rotary evaporator. For fine purification the residue is chromatographed over silica gel 60 by means of subatmospheric pressure (eluent: cyclohexane/ethyl acetate 40/10) and 265 mg (58% of theory) of product are obtained.

HPLC (method 10): $R_t$=3.70 min;
MS (ESI+): m/z=315 (M+H)$^+$
$^1$H NMR (300 MHz, CDCl$_3$): δ=1.01 (d, 3H), 1.09 (d, 3H), 1.27 (m, 6H), 1.45 (s, 9H), 2.78-2.95 (m, 3H), 3.03 (m, 1H), 3.53-3.83 (m, 3H: including 3.78 (q, 1H)), 4.18 (q, 2H).

Example 62A tert-Butyl (3RS,5SR)-4-(2-ethoxy-1,1-dimethyl-2-oxoethyl)-3,5-dimethylpiperazine-1-carboxylate

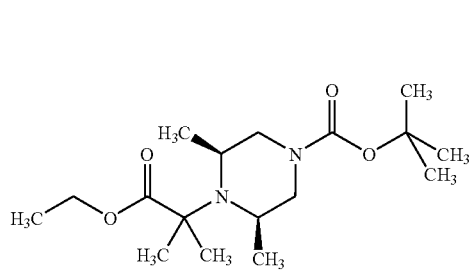

70 mg of the title compound are obtained as a second product from the experiment described under Example 61A.

HPLC (method 10): $R_t$=4.02 min;

MS (ESI+): m/z=329 (M+H)$^+$

Example 63A

Ethyl 2-[(2RS,6SR)-2,6-dimethylpiperazin-1-yl]propanoate bistrifluoroacetate

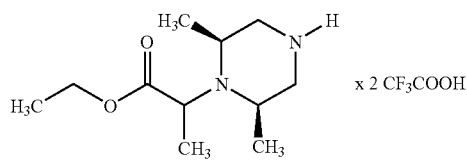

120.0 mg (0.38 mmol) of the compound from Example 61A are dissolved in 2 ml of a mixture of trifluoroacetic acid/dichloromethane (1/1) and the mixture is stirred at room temperature for 20 minutes. For the work-up, the solvent is removed completely on a rotary evaporator, and after drying under high vacuum 155 mg (92% of theory) of product are obtained.

MS (ESI+): m/z=214 (M+H)$^+$;

$^1$H NMR (400 MHz, CDCl$_3$): δ=1.31-1.43 (m, 6H), 1.57 (d, 3H), 1.69 (d, 3H), 3.55 (m, 2H), 3.92-4.48 (m, 7H).

Example 64A

Ethyl 2-[(2RS,6SR)-2,6-dimethylpiperazin-1-yl]-2-methylpropanoate bistrifluoroacetate

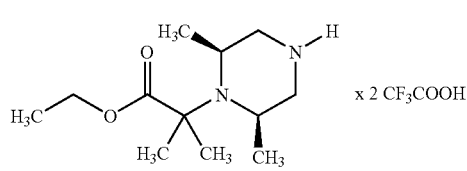

The title compound is obtained from Example 62A in analogy to Example 63A. It is directly reacted further to give Example 66A.

Example 65A

1-Cyclopropyl-7-[(3RS,5SR)-4-(2-ethoxy-1-methyl-2-oxoethyl)-3,5-dimethylpiperazin-1-yl]-6-fluoro-8-methoxy-4-oxo-1,4-dihydroquinoline-3-carboxylic acid

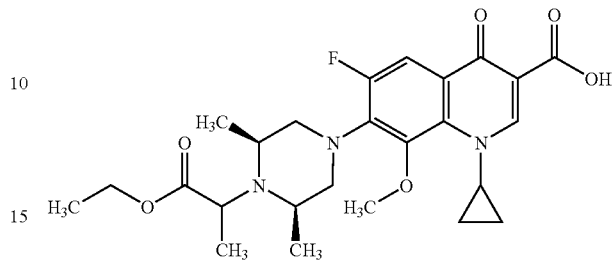

In order to liberate the base from the compound of Example 63A, 120.2 mg (0.35 mmol) of the compound from Example 63A are provided in 2 ml of dichloromethane/acetonitrile (1/1), subsequently, 400 mg of tris(2-aminoethyl)amine-polystyrene are added, the mixture is stirred at room temperature for 20 minutes and filtered, the residue is washed with dichloromethane, and the dichloromethane is distilled off on a rotary evaporator under a subatmospheric pressure of 500 mbar. To this solution 155.0 mg (0.35 mmol) of (1-cyclopropyl-6-7-difluoro-8-methoxy-4-oxo-1,4-dihydroquinolin-3-yl)carbonyl difluoridoborate (for preparation: see Journal of Medicinal Chemistry 1995, 38(22), 4478-4487) are added, and the reaction is stirred at 50° C. overnight. The solvent is removed completely on a rotary evaporator, 2.5 ml of triethylamine and 5.0 ml of ethanol are added to the residue, and the mixture is stirred under reflux for 1 h. The solvents are removed on a rotary evaporator, and after fine purification of the residue via preparative RP-HPLC (method 5) 45 mg (26% of theory) of product are obtained.

HPLC (method 9): $R_t$=3.85 min;

MS (ESI$^+$): m/z=490 (M+H)$^+$;

$^1$H NMR (400 MHz, CDCl$_3$): δ=0.93-1.10 (m, 5H: including 1.08 (d, 3H)), 1.12-1.24 (m, 5H: including 1.18 (d, 3H)), 1.28-1.39 (m, 6H), 3.10 (m, 2H), 3.21 (m, 2H), 3.35 (m, 1H), 3.49 (m, 1H), 3.73 (s, 3H), 3.89 (q, 1H), 4.01 (m, 1H), 4.22 (q, 2H), 7.87 (d, 1H), 8.81 (s, 1H).

Example 66A

1-Cyclopropyl-7-[(3RS,5SR)-4-(2-ethoxy-1,1-dimethyl-2-oxoethyl)-3,5-dimethylpiperazin-1-yl]-6-fluoro-8-methoxy-4-oxo-1,4-dihydroquinoline-3-carboxylic acid

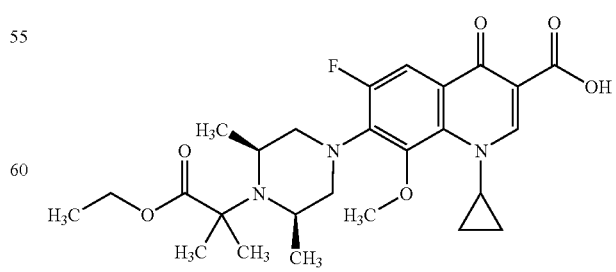

The title compound is prepared from the compound from Example 64A in analogy to Example 65A.

LC-MS (method 1): $R_t$=2.13 min;
MS (ES+): m/z=504 (M+H)$^+$.

EXEMPLARY EMBODIMENTS

General Working Instructions 1

Alkylation of the Piperazine Derivatives

The piperazine derivative (1 eq.), 2.5 eq. of alkylating agent, 4.5 eq. of potassium carbonate and 0.3 equivalents of potassium iodide are stirred in acetonitrile under reflux overnight. The cooled mixture is diluted with dichloromethane and subsequently washed twice with water, the organic phase is dried over sodium sulfate and filtered, and the solvent is removed completely on a rotary evaporator. From the residue, the target compound is obtained after separation via preparative RP-HPLC. Ethyl chloroacetate, ethyl bromoacetate or ethyl 2-bromopropanoate are used as alkylating agents.

Example 1

Ethyl{(2RS,6SR)-4-[3-{[(2,4-dichlorobenzyl)amino]carbonyl}-6-fluoro-8-methoxy-4-oxo-1-(2,2,2-trifluoroethyl)-1,4-dihydroquinolin-7-yl]-2,6-dimethylpiperazin-1-yl}ethanoate hydroformate

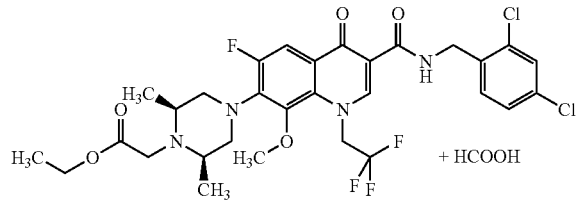

810.0 mg (1.29 mmol) of N-(2,4-dichlorobenzyl)-7-[(3RS,5SR)-3,5-dimethylpiperazin-1-yl]-6-fluoro-8-methoxy-4-oxo-1-(2,2,2-trifluoroethyl)-1,4-dihydroquinoline-3-carboxamide hydrochloride (Example 38A), 396.5 mg (3.24 mmol) of ethyl chloroacetate, 64.5 mg (0.39 mmol) of potassium iodide and 804.9 mg (5.82 mmol) of potassium carbonate are stirred under reflux in 20 ml of acetonitrile overnight. The Work-up takes place in analogy to the general working instructions 1, and after purification via preparative RP-HPLC (method 5) 1050 mg of the target compound are obtained.

HPLC (method 9): $R_t$=4.87 min,
MS (ESI+)=675 (M+H)$^+$
$^1$H NMR (300 MHz, CDCl$_3$): δ=1.15 (d, 6H), 1.41 (t, 3H), 2.99-3.14 (m, 2H), 3.18-3.37 (m, 4H), 3.66 (s, 2H), 3.83 (s, 3H), 4.19 (q, 2H), 4.69 (d, 2H), 5.26 (q, 2H), 7.21 (dd, 1H), 7.38 (m, 2H), 7.90 (d, 1H), 8.03 (s, 1H), 8.58 (s, 1H), 10.28 (t, 1H).

Example 2

Ethyl((2RS,6SR)-4-{3-{[(2,4-dichlorobenzyl)amino]carbonyl}-6-fluoro-1-[(1S,2R)-2-fluorocyclopropyl]-8-methoxy-4-oxo-1,4-dihydroquinolin-7-yl}-2,6-dimethylpiperazin-1-yl)ethanoate

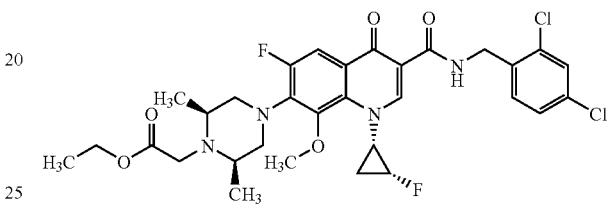

From 40 mg (0.05 mmol) of N-(2,4-dichlorobenzyl)-7-[(3RS,5SR)-3,5-dimethylpiperazin-1-yl]-6-fluoro-1-[(1S,2R)-2-fluorocyclopropyl]-8-methoxy-4-oxo-1,4-dihydroquinoline-3-carboxamide (Example 57A), 7 µl (11.1 mg, 0.07 mmol) of ethyl bromoacetate, 17.3 mg (0.10 mmol) of potassium iodide, 8 µl (6.1 mg, 0.05 mmol) of N,N-diisopropylethylamine and 16.4 mg (0.12 mmol) of potassium carbonate 10 mg of the target product are obtained, as described in general working instructions 1 for the alkylation of the piperazine derivatives, without further purification processes.

LC-MS (method 3): $R_t$=2.41 min,
MS (ES+)=651 (M+H)$^+$

The following Examples 3 to 8 are prepared in accordance with general working instructions 1, from the starting materials indicated.

| Example No. | Structure | Starting materials Ex. No. | Analytical data LC-MS (method)/ measurement values HPLC (method)/ measurement value MS (method)/ measurement value NMR spectrum |
|---|---|---|---|
| 3 | 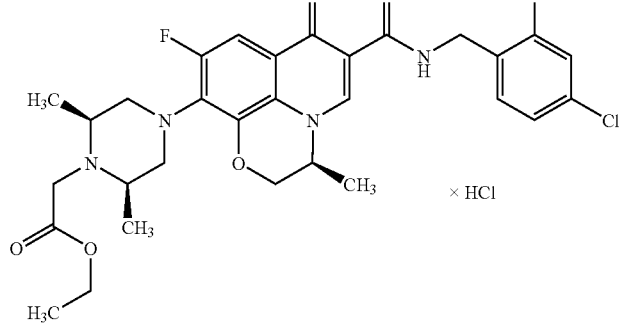 | 59A | LC-MS (method 3): $R_t$ = 2.19 min MS (ES+): m/z = 619 (M + H)$^+$ |

-continued

| Example No. | Structure | Starting materials Ex. No. | Analytical data LC-MS (method)/ measurement values HPLC (method)/ measurement value MS (method)/ measurement value NMR spectrum |
|---|---|---|---|
| 4 | 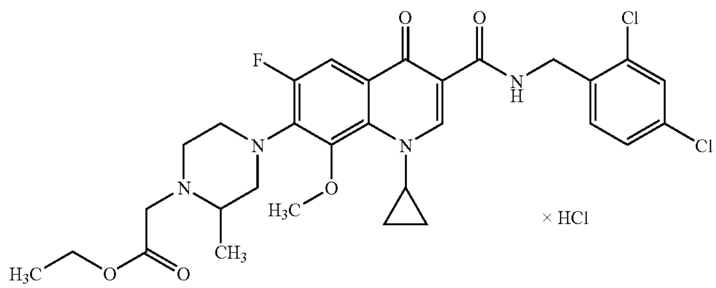 | 48A | LC-MS (method 1): $R_t$ = 2.21 min MS (ES+): m/z = 619 (M + H)$^+$ |
| 5 | 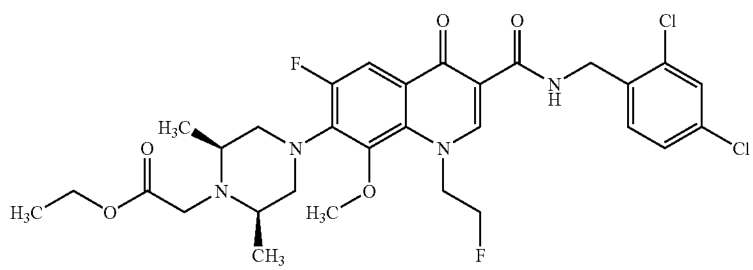 | 51A | HPLC (method 9): $R_t$ = 4.66 min MS (ESI): m/z = 639 (M + H)$^+$ |
| 6 | 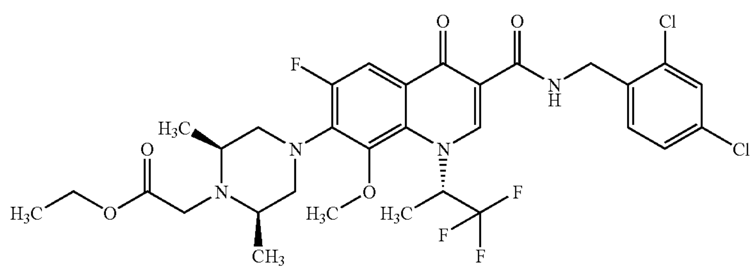 | 53A | HPLC (method 9): $R_t$ = 4.93 min MS (ESI): m/z = 689 (M + H)$^+$ |
| 7 | 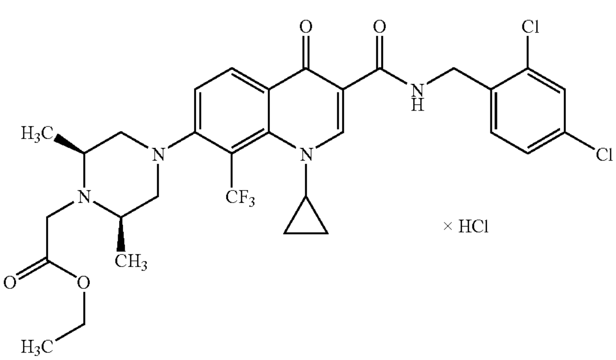 | 56A | LC-MS (method 2): $R_t$ = 2.78 min MS (ES+): m/z = 653 (M + H)$^+$ |

| Example No. | Structure | Starting materials Ex. No. | Analytical data LC-MS (method)/measurement values HPLC (method)/measurement value MS (method)/measurement value NMR spectrum |
|---|---|---|---|
| 8 | 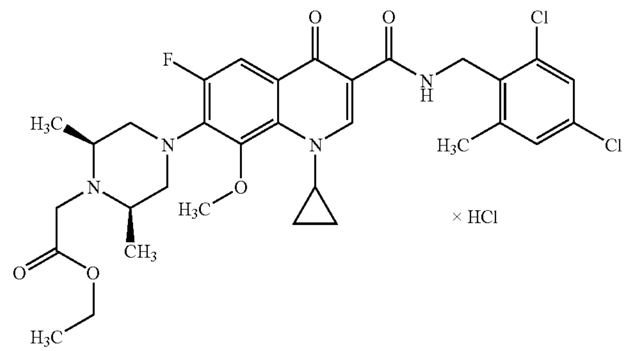 | 41A | LC-MS (method 3): $R_t$ = 2.56 min MS (ES+): m/z = 647 (M + H)$^+$ |

Example 9

Ethyl 4-[3-{1-cyclopropyl-[(2,4-dichlorobenzyl)amino]carbonyl}-1-fluoro-8-methoxy-4-oxo-1,4-dihydroquinolin-7-yl]-(2RS,6SR)-2,6-dimethylpiperazin-1-yl}ethanoate hydrochloride

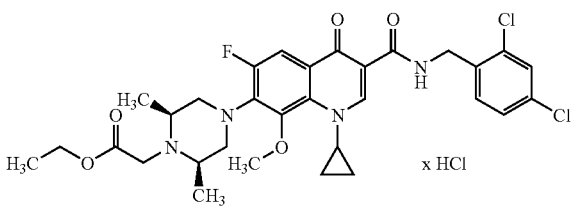

1 g of the compound from Example 39A is heated under reflux with 343 mg of ethyl bromoacetate, 312 mg of potassium iodide and 590 mg of potassium carbonate in 60 ml of acetonitrile for 2 h. After cooling, the reaction mixture is separated by preparative HPLC (method 6). 862 mg (75% of theory) of the title compound are obtained.

LC-MS (method 2): $R_t$=2.39 min, MS (ESI): m/z=633 (M+H)$^+$.

$^1$H NMR (400 MHz, DMSO-d$_6$): δ=0.98 (m, 2H), 1.12 (m, 2H), 1.29 (t, 3H), 1.33 (d, 6H), 3.35-3.69 (m, 4H), 3.72-3.90 (m, 5H: including 3.79 (s, 3H)), 4.11 (m, 1H), 4.23-4.51 (m, 4H: including 4.29 (q, 2H)), 4.59 (d, 2H), 7.39 (d, 1H), 7.42 (dd, 1H), 7.53 (d, 1H), 7.78 (d, 1H), 8.69 (s, 1H), 10.22 (t, 1H).

The following Examples 10 to 22 are prepared in accordance with general working instructions 1, from the starting materials indicated.

| Example No. | Structure | Starting materials Ex. No. | Analytical data LC-MS (method)/measurement values HPLC (method)/measurement value MS (method)/measurement value NMR spectrum |
|---|---|---|---|
| 10 | 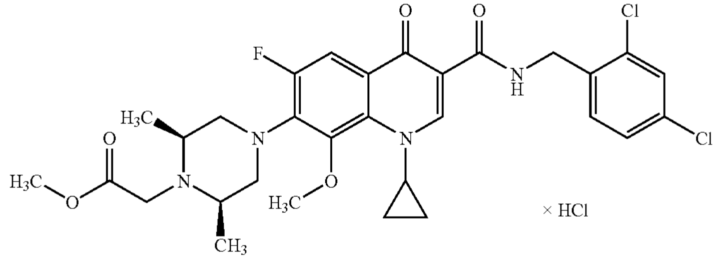 | 39A | LC-MS (method 1): $R_t$ = 2.31 min MS (ES+): m/z = 619 (M + H)$^+$ |

-continued

| Example No. | Structure | Starting materials Ex. No. | Analytical data LC-MS (method)/measurement values HPLC (method)/measurement value MS (method)/ measurement value NMR spectrum |
|---|---|---|---|
| 11 | 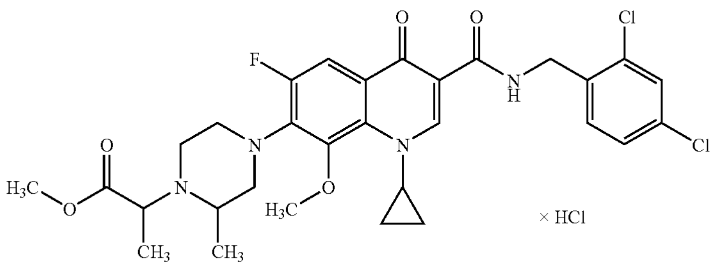 | 48A | LC-MS (method 3): $R_t$ = 2.16/2.47 min MS (ES+): m/z = 619 (M + H)$^+$ |
| 12 | 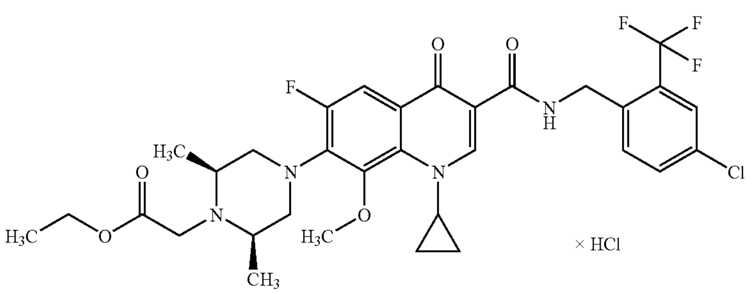 | 42A | LC-MS (method 3): $R_t$ = 2.55 min MS (ES+): m/z = 667 (M + H)$^+$ |
| 13 | 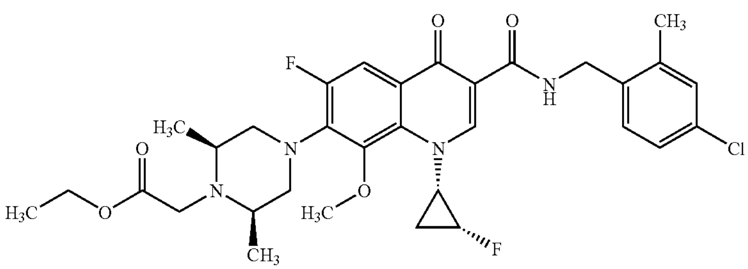 | 52A | LC-MS (method 3): $R_t$ = 2.35 min MS (ES+): m/z = 631 (M + H)$^+$ |
| 14 | 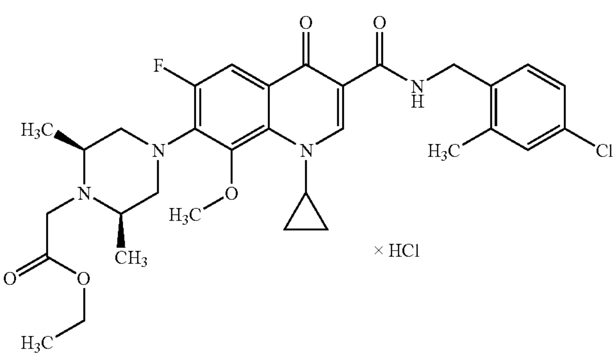 | 40A | LC-MS (method 1): $R_t$ = 2.41 min MS (ES+): m/z = 613 (M + H)$^+$ |

-continued

| Example No. | Structure | Starting materials Ex. No. | Analytical data LC-MS (method)/measurement values HPLC (method)/measurement value MS (method)/ measurement value NMR spectrum |
|---|---|---|---|
| 15 | 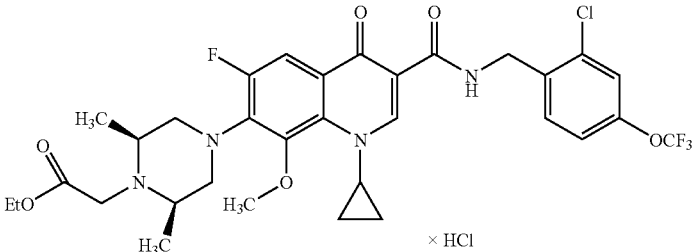 | 43A | LC-MS (method 2): $R_t$ = 2.46 min MS (ES+): m/z = 683 (M + H)$^+$ |
| 16 | 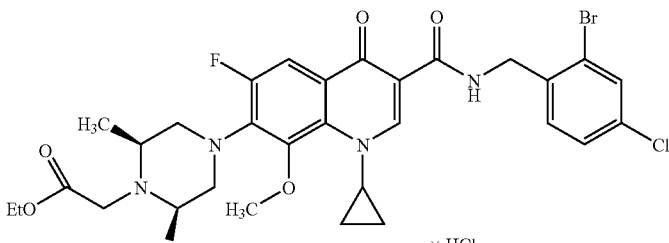 | 44A | LC-MS (method 2): $R_t$ = 2.38 min MS (ES+): m/z = 677/679 (M + H)$^+$ |
| 17 | 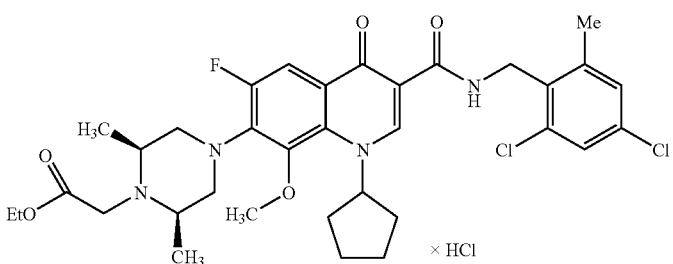 | 54A | LC-MS (method 3): $R_t$ = 2.91 min MS (ES+): m/z = 675 (M + H)$^+$ |
| 18 | 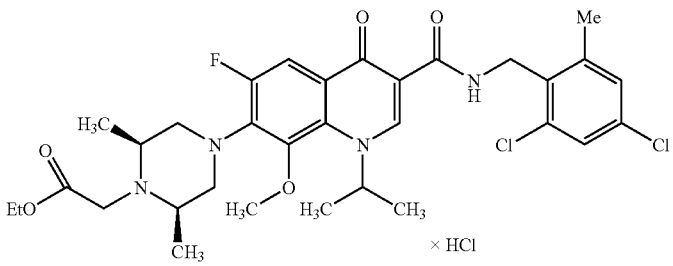 | 55A | LC-MS (method 2): $R_t$ = 2.54 min MS (ES+): m/z = 649 (M + H)$^+$ |
| 19 | 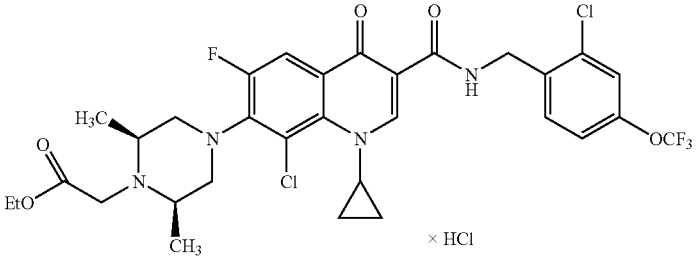 | 47A | LC-MS (method 11): $R_t$ = 2.58 min MS (ES+): m/z = 687 (M + H)$^+$ |

| Example No. | Structure | Starting materials Ex. No. | Analytical data LC-MS (method)/measurement values HPLC (method)/measurement value MS (method)/ measurement value NMR spectrum |
|---|---|---|---|
| 20 | 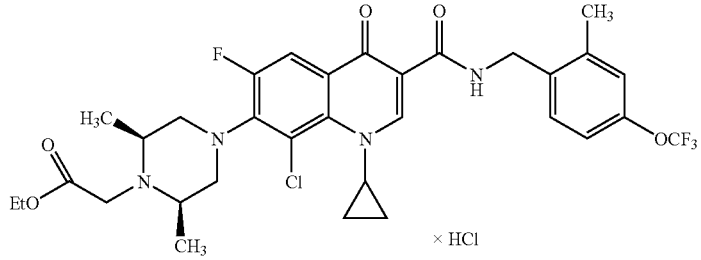 | 46A | LC-MS (method 2): $R_t$ = 2.52 min MS (ES+): m/z = 667 (MH)$^+$ |
| 21 | 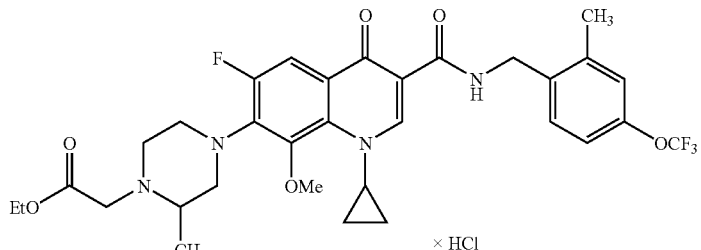 | 49A | LC-MS (method 2): $R_t$ = 2.27 min MS (ES+): m/z = 649 (M + H)$^+$ |
| 22 | 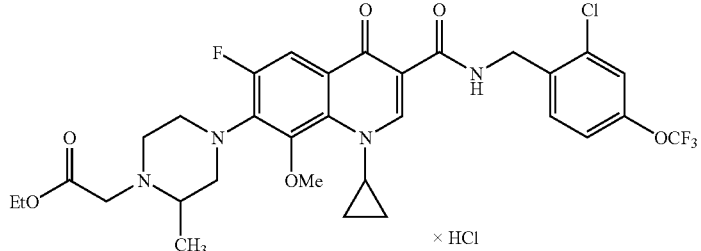 | 50A | LC-MS (method 2): $R_t$ = 2.32 min MS (ES+): m/z = 669 (M + H)$^+$ |

Example 23

Ethyl{(2RS,6SR)-4-[3-{[(2,4-dichlorobenzyl)amino]carbonyl}-6-fluoro-8-methoxy-4-oxo-1-(2,2,2-trifluoroethyl)-1,4-dihydroquinolin-7-yl]-2,6-dimethylpiperazin-1-yl}(oxo)ethanoate

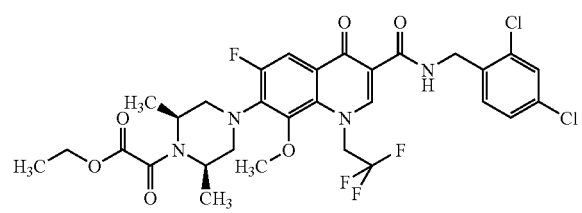

200 mg of the compound from Example 37A are dissolved in 3 ml of dichloromethane and 0.26 ml of pyridine and 71 µl of ethyl oxalate chloride are then added. The mixture is stirred at RT for 3 h. For the work-up, the mixture is diluted with ethyl acetate, and extracted by shaking twice with water, once with a saturated sodium hydrogen carbonate solution and once with a saturated sodium chloride solution. The organic phase is dried over sodium sulfate, concentrated in vacuo, and dried under high vacuum. 220 mg of the title compound are obtained.

LC-MS (method 3): $R_t$=3.19 min

MS (ES+): m/z=689 (M+H)$^+$.

Example 24

1-Cyclopropyl-N-(2,4-dichlorobenzyl)-7-[(3RS,5SR)-3,5-dimethyl-4-(2-ethoxycarbonylethyl)piperazin-1-yl]-6-fluoro-8-methoxy-4-oxo-1,4-dihydroquinoline-3-carboxamide hydrochloride

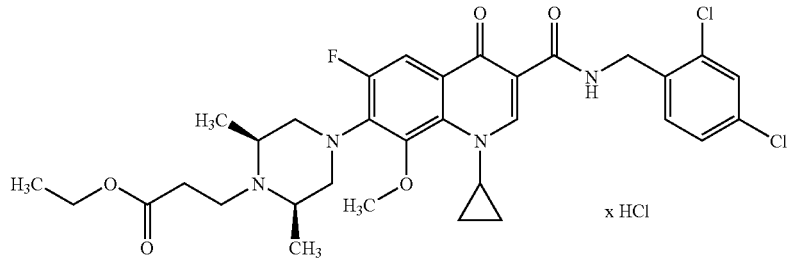

150 mg of the compound from Example 39A are provided with 4 eq. of lithium perchlorate and ethyl acrylate in excess (approximately 400 µl) is added. The suspension is stirred at RT for 12 h and then purified directly via preparative HPLC (method 6). 79 mg (42% of theory) of the title compound are obtained.

LC-MS (method 3): $R_t$=2.09 min

MS (ES+): m/z=647 (M+H)$^+$ $^1$H NMR (400 MHz, DMSO-$d_6$): δ=0.97 (m, 2H), 1.11 (m, 2H), 1.23 (t, 3H), 1.37 (d, 6H), 2.94 (m, 2H), 3.43-3.68 (m, 8H), 3.71 (s, 3H), 4.09 (m, 1H), 4.14 (q, 2H), 4.58 (d, 2H), 7.38 (d, 1H), 7.42 (dd, 1H), 7.64 (d, 1H), 7.76 (d, 1H), 8.79 (s, 1H), 10.21 (t, 1H).

Example 25

N-{[(2RS,6SR)-4-(1-Cyclopropyl-3-{[(2,4-dichlorobenzyl)amino]carbonyl}-6-fluoro-8-methoxy-4-oxo-1,4-dihydroquinolin-7-yl)-2,6-dimethylpiperazin-1-yl]carbonyl}glycine ethyl ester

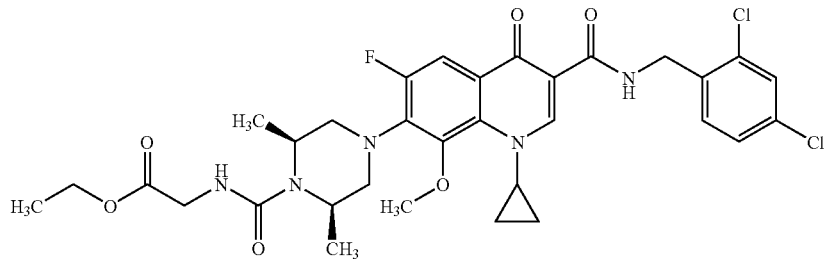

100 mg (0.18 mmol) of the compound from Example 39A are added to a solution of 25 mg (0.22 mmol) of ethyl isocyanatoacetate in 5 ml of dichloromethane. The reaction mixture is stirred at RT overnight. After the removal of the solvent on a rotary evaporator, the residue is purified by RP-HPLC (method 6). 73 mg (59% of theory) of the title compound are obtained.

LC-MS (method 3): $R_t$=2.88 min

MS (ESI): m/z=676 (M+H)$^+$

Example 26

N-{[(2RS,6SR)-4-(1-Cyclopropyl-3-{[(2,4-dichlorobenzyl)amino]carbonyl}-6-fluoro-8-methoxy-4-oxo-1,4-dihydroquinolin-7-yl)-2,6-dimethylpiperazin-1-yl]carbonyl}alanine acid ethyl ester

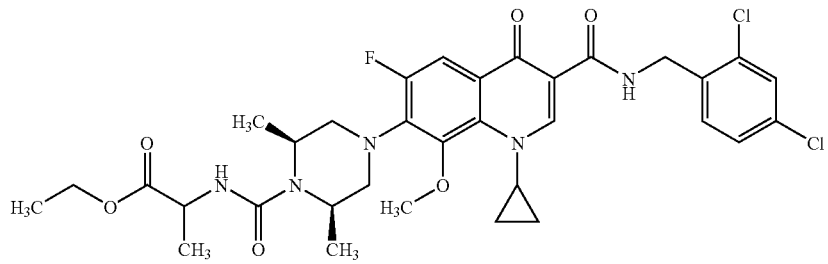

The title compound is prepared in analogy to Example 25, from the compound from Example 39A and 1-ethoxycarbonylethyl isocyanate.

LC-MS (method 2): $R_t$=2.80 min
MS (ESI): m/z=690 (M+H)$^+$

Example 27

Ethyl 2-[(2RS,6SR)-4-(1-cyclopropyl-3-{[(2,4-dichlorobenzyl)amino]carbonyl}-6-fluoro-8-methoxy-4-oxo-1,4-dihydroquinolin-7-yl)-2,6-dimethylpiperazin-1-yl]propanoate

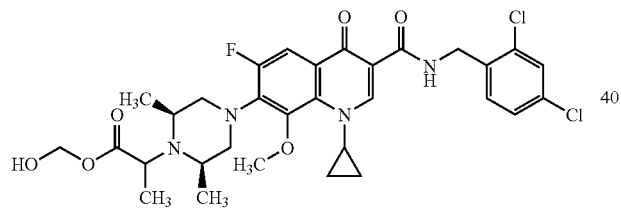

43.0 mg (0.08 mmol) of the compound from Example 65A, 28.3 mg (0.16 mmol) of 2,4-dichlorobenzylamine and 77 µl (57.1 mg, 0.44 mmol) of N,N-diisopropylethylamine are provided in 5.2 ml of N,N-dimethylformamide, 104.5 mg (0.20 mmol) of PyBOP are added, and the mixture is stirred at room temperature for 3 h. For the work-up, ethyl acetate is added to the reaction mixture and the mixture is extracted by shaking twice with water, and the combined aqueous phases are extracted with ethyl acetate, the combined organic phases are dried over sodium sulfate and filtered, and the solvent is removed completely on a rotary evaporator. After fine purification of the obtained residue via preparative RP-HPLC (method 5) 48 mg (92% of theory) of product are obtained.

LC-MS (method 2): $R_t$=2.22 min, MS (ES+): m/z=647 (M+H)$^+$;

$^1$H NMR (400 MHz, CDCl$_3$): δ=0.94 (m, 2H), 1.06 (d, 3H), 1.11-1.21 (m, 5H: including 1.18 (d, 3H)), 1.28-1.39 (m, 6H), 2.98 (m, 1H), 3.08 (m, 1H), 3.18 (m, 2H), 3.31 (m, 1H), 3.43 (m, 1H), 3.72 (s, 3H), 3.89 (q, 1H), 3.95 (m, 1H), 4.23 (q, 2H), 4.69 (d, 2H), 7.18 (dd, 1H), 7.38 (s, 1H), 7.40 (d, 1H), 7.85 (d, 1H), 8.82 (s, 1H), 10.39 (t, 1H).

General Working Instructions 2

Hydrolysis of the Esters to Carboxylic Acids 1.0 equivalent of ester and 5.0 equivalents of a 1M lithium hydroxide solution are stirred in dioxane at room temperature overnight. For the work-up, the reaction is diluted with water, subsequently adjusted to pH 3 using 1M hydrochloric acid, and extracted three times with dichloromethane, and the combined organic phases are dried over sodium sulfate. The sodium sulfate is filtered off and the solvent is removed completely on a rotary evaporator. After fine purification via preparative RP-HPLC (method 5 or 6) the target compound is obtained.

Example 28

{(2RS,6SR)-4-[3-{[(2,4-Dichlorobenzyl)amino]carbonyl}-6-fluoro-8-methoxy-4-oxo-1-(2,2,2-trifluoroethyl)-1,4-dihydroquinolin-7-yl]-2,6-dimethylpiperazin-1-yl}ethanoic acid hydroformate

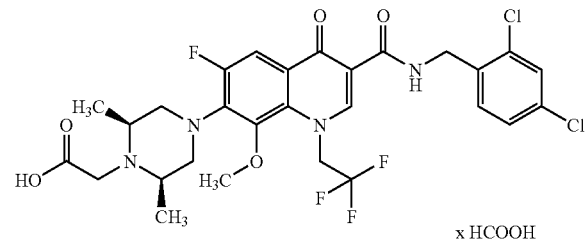

45.0 mg (0.06 mmol) of the compound from Example 1 are dissolved in 1 ml of dioxane, and 0.31 ml (0.31 mmol) of a 1M lithium hydroxide solution are subsequently added and the mixture is stirred at room temperature overnight. For the work-up, the solvent is removed on a rotary evaporator, the residue is taken up in water and acidified (pH 3) using 1M hydrochloric acid, and the precipitate formed is dissolved with a little dimethyl sulfoxide. After fine purification via preparative RP-HPLC (method 5), 38 mg of the target compound are obtained from the solution.

HPLC (method 9): $R_t$=4.62 min,
MS (ESI+)=647 (M+H)$^+$.

$^1$H NMR (300 MHz, DMSO-$d_6$): δ=1.04 (m, 6H), 2.90-3.85 (m, 11H: including 3.78 (s, 3H)), 4.69 (d, 2H), 5.70 (m, 2H), 7.36-7.48 (m, 2H), 7.65 (d, 2H), 7.78 (d, 1H), 8.14 (s, 1H), 8.83 (s, 1H), 10.14 (t, 1H).

Example 29

4-[3-{1-Cyclopropyl-[(2,4-dichlorobenzyl)amino]carbonyl}-1-fluoro-8-methoxy-4-oxo-1,4-dihydroquinolin-7-yl]-(2RS,6SR)-2,6-dimethylpiperazin-1-yl}ethanoic acid hydrochloride

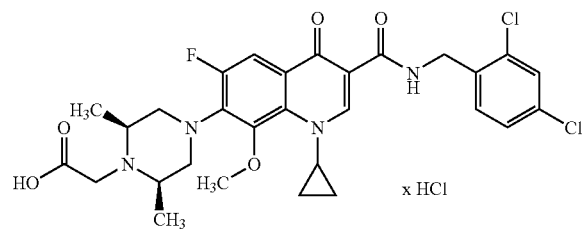

200 mg of the compound from Example 9 are dissolved in 5 ml of dioxane, 5 ml of a 1M lithium hydroxide solution are subsequently added and the mixture stirred at 50° C. for 2 h. For the work-up, the solvent is removed on a rotary evaporator, the residue is taken up in water and acidified (pH 3-4) using 1M hydrochloric acid. The precipitate formed is collected by filtration, washed with water and dried under high vacuum. 140 mg 73% of theory) of the title compound are obtained.

LC-MS (method 3): $R_t$=2.10 min, MS (ESI): m/z=605 (M+H)$^+$.

$^1$H NMR (300 MHz, DMSO-$d_6$): δ=0.99 (m, 2H), 1.18 (m, 2H), 1.38 (d, 6H), 3.46 (m, 2H), 3.55 (m, 2H), 3.70 (s, 3H), 3.78 (m, 4H), 3.95 (m, 1H), 4.68 (d, 2H), 7.20 (dd, 1H), 7.38 (m, 2H), 7.86 (d, 1H), 1H), 8.84 (s, 1H), 10.28 (t, 1H).

Examples 30 to 49 listed in the table below are obtained in analogy to Example 28, in accordance with general working instructions 2.

| Example No. | Structure | Starting materials Ex. No. | Analytical data LC-MS (method)/measurement values HPLC (method)/measurement value MS (method)/measurement value |
|---|---|---|---|
| 30 | 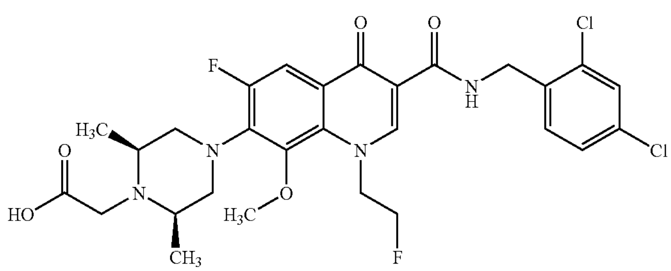 | 5 | HPLC (method 9): $R_t$ = 4.41 min MS (ESI): m/z = 611 (M + H)$^+$ |
| 31 | 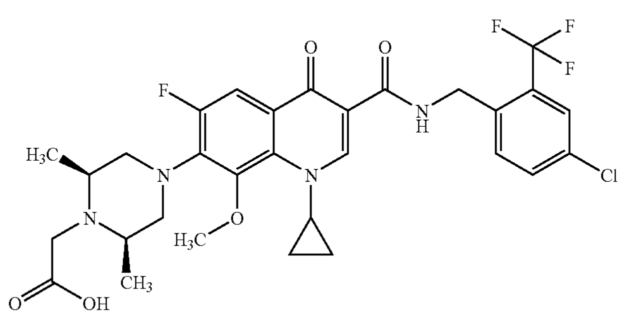 | 12 | LC-MS (method 3): $R_t$ = 2.20 min MS (ESI): m/z = 639 (M + H)$^+$ |

-continued

| Example No. | Structure | Starting materials Ex. No. | Analytical data LC-MS (method)/ measurement values HPLC (method)/measurement value MS (method)/measurement value |
|---|---|---|---|
| 32 | 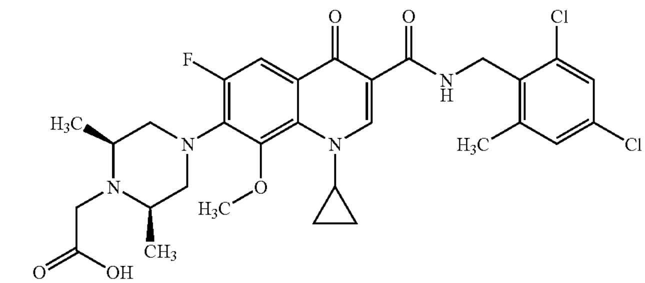 | 8 | LC-MS (method 3): $R_t$ = 2.20 min MS (ESI): m/z = 619 (M + H)$^+$ |
| 33 | 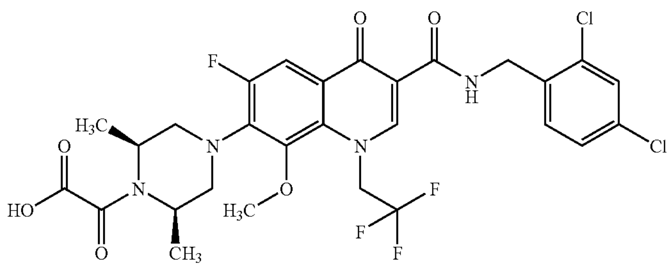 | 23 | LC-MS (method 3): $R_t$ = 3.19 min MS (ESI): m/z = 689 (M + H)$^+$ |
| 34 | 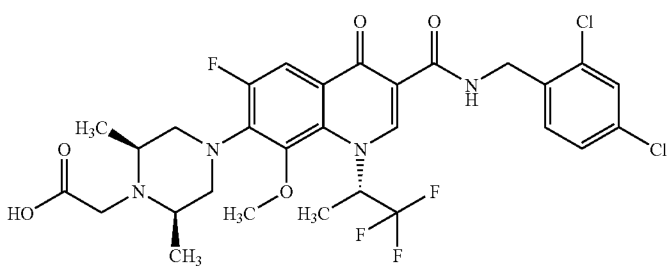 | 6 | HPLC (method 9): $R_t$ = 4.69 min MS (ESI+): m/z = 662 (M + H)$^+$ |
| 35 | 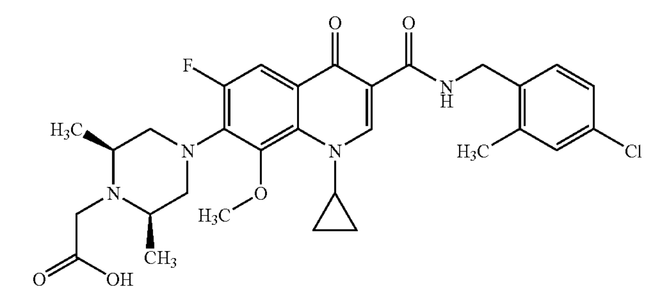 | 14 | LC-MS (method 3): $R_t$ = 2.07 min MS (ES+): m/z = 585 (MH)$^+$ |
| 36 | 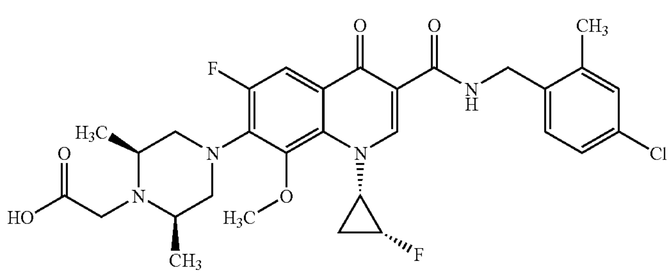 | 13 | LC-MS (method 3): $R_t$ = 2.07 min MS (ESI+): m/z = 602 (M + H)$^+$ |

-continued

| Example No. | Structure | Starting materials Ex. No. | Analytical data LC-MS (method)/ measurement values HPLC (method)/measurement value MS (method)/measurement value |
|---|---|---|---|
| 37 | 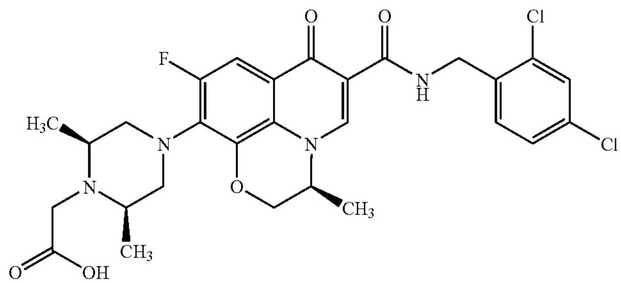 | 3 | LC-MS (method 3): $R_t$ = 2.19 min MS (ESI): m/z = 619 (M + H)$^+$ |
| 38 | 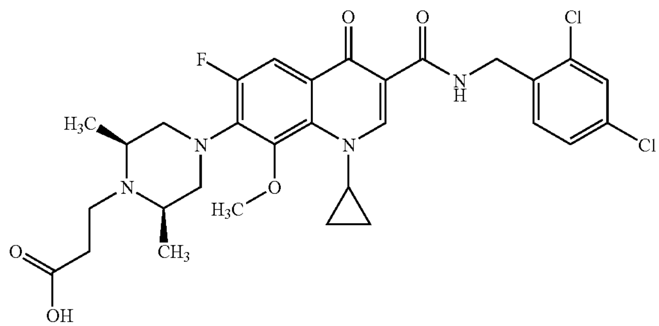 | 24 | LC-MS (method 1): $R_t$ = 1.93 min MS (ES+): m/z = 619 (M + H)$^+$ |
| 39 | 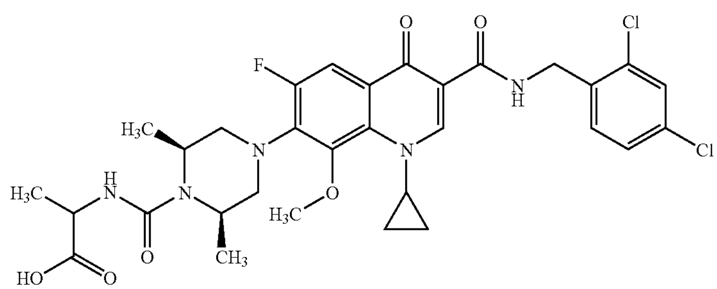 | 26 | LC-MS (method 1): $R_t$ = 2.64 min MS (ES+): m/z = 662 (M + H)$^+$ |
| 40 | 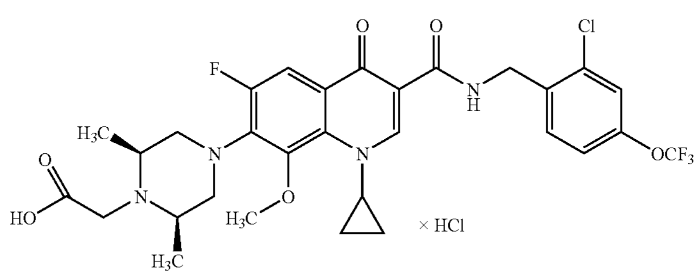 | 15 | LC-MS (method 1): $R_t$ = 2.21 min MS (ES+): m/z = 655 (M + H)$^+$ |
| 41 | 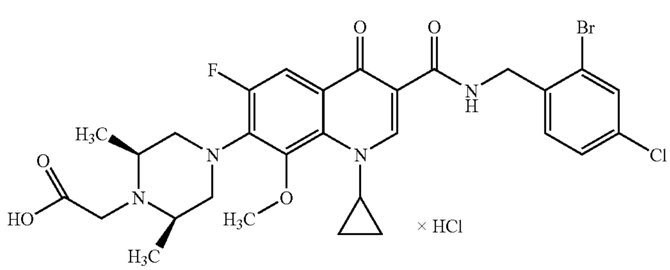 | 16 | LC-MS (method 1): $R_t$ = 2.13 min MS (ES+): m/z = 649/651 (M + H)$^+$ |

-continued

| Example No. | Structure | Starting materials Ex. No. | Analytical data LC-MS (method)/ measurement values HPLC (method)/measurement value MS (method)/measurement value |
|---|---|---|---|
| 42 | 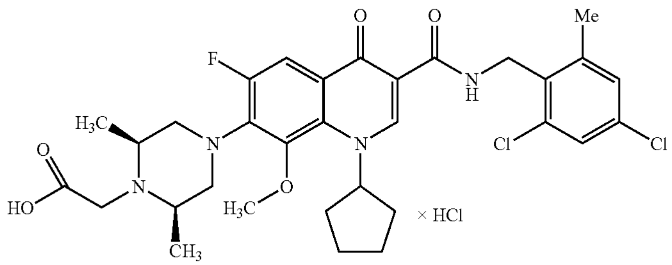 | 17 | LC-MS (method 1): $R_t = 2.36$ min MS (ES+): m/z = 647 (M + H)$^+$ |
| 43 | 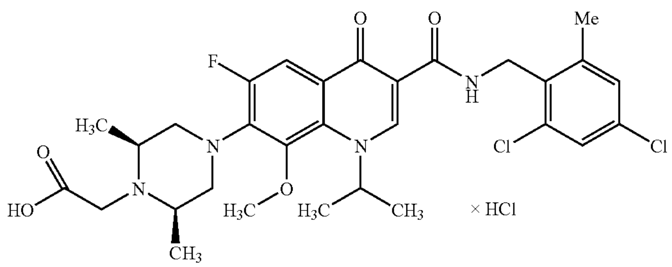 | 18 | LC-MS (method 1): $R_t = 2.22$ min MS (ES+): m/z = 621 (M + H)$^+$ |
| 44 | 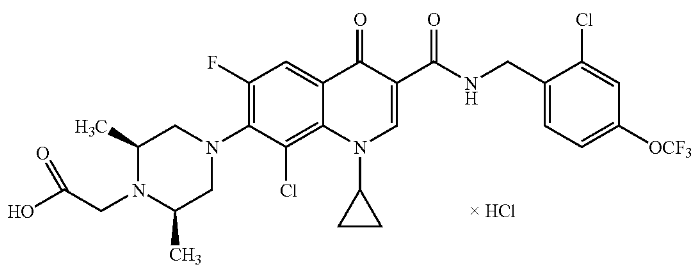 | 19 | LC-MS (method 1): $R_t = 2.23$ min MS (ES+): m/z = 659 (M + H)$^+$ |
| 45 | 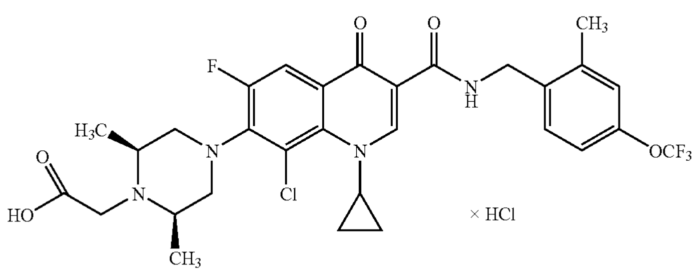 | 20 | LC-MS (method 1): $R_t = 2.18$ min MS (ES+): m/z = 639 (M + H)$^+$ |
| 46 | 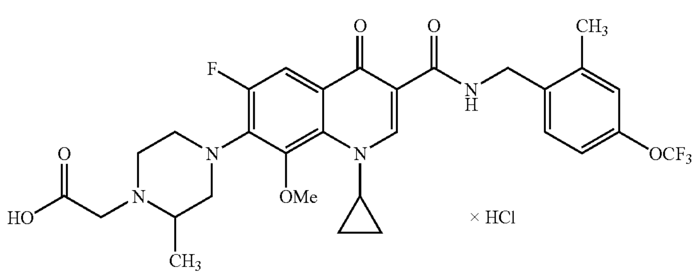 | 21 | LC-MS (method 1): $R_t = 2.13$ min MS (ES+): m/z = 621 (M + H)$^+$ |

| Example No. | Structure | Starting materials Ex. No. | Analytical data LC-MS (method)/ measurement values HPLC (method)/measurement value MS (method)/measurement value |
|---|---|---|---|
| 47 | 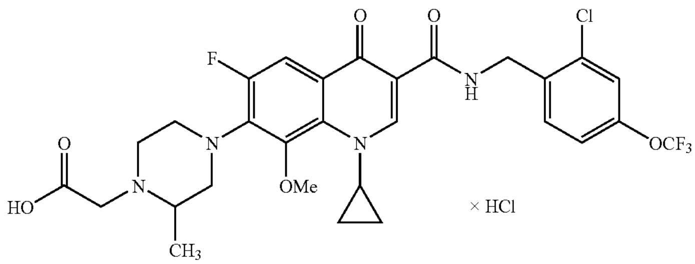 | 22 | LC-MS (method 1): $R_t$ = 2.17 min MS (ES+): m/z = 641 (M + H)+ |
| 48 | 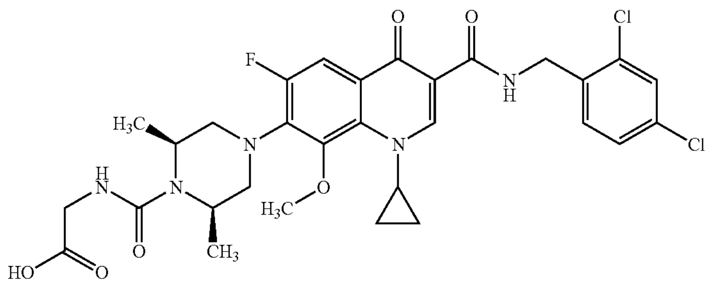 | 25 | LC-MS (method 3): $R_t$ = 2.88 min MS (ES+): m/z = 676 (M + H)+ |
| 49 | 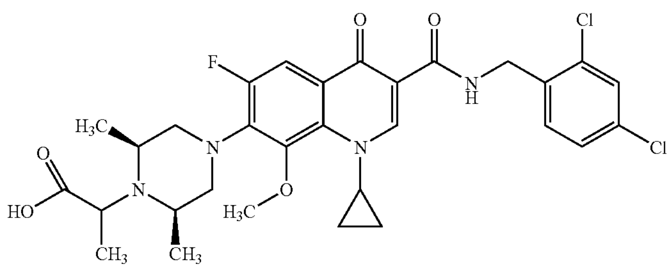 | 27 | HPLC (method 9): $R_t$ = 4.31 min MS (ESI): m/z = 619 (M + H)+ |

Example 50

Ethyl 2-[2RS,6SR)-4-(1-cyclopropyl-3-{[(2,4-dichlorobenzyl)amino]carbonyl}-6-fluoro-8-methoxy-4-oxo-1,4-dihydroquinolin-7-yl)-2,6-dimethylpiperazin-1-yl]-2-methylpropanoate

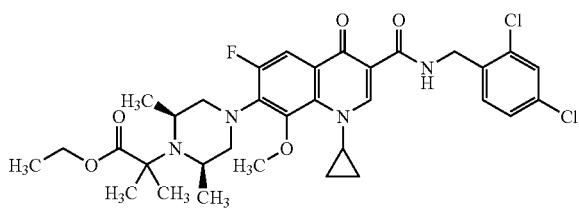

The title compound is prepared in analogy to Example 27, from the compound from Example 66A and 2,4-dichlorobenzylamine.

LC-MS (method 1): $R_t$=3.02 min.

MS (ES+): m/z=661 (M+H)+

B. Assessment of the Physiological Activity

The in vitro activity of the compounds of the invention can be shown in the following assays:

Anti-HCMV (Anti-Human Cytomegalovirus) Cytopathogenicity Tests

The test compounds are employed as 50 millimolar (mM) solutions in dimethyl sulfoxide (DMSO). Ganciclovir®, Foscamet® and Cidofovir® are used as reference compounds. After the addition of in each case 2 µl of the 50, 5, 0.5 and 0.05 mM DMSO stock solutions to 98 µl portions of cell culture medium in row 2 A-H for duplicate determinations, 1:2 dilutions are carried out with 50 µl portions of medium up to row 1 1 of the 96-well plate. The wells in rows 1 and 12 each contain 50 µl of medium. 150 µl of a suspension of 1×10⁴ cells (human prepuce fibroblasts [NHDF]) are then pipetted into each of the wells (row I=cell control) and, in rows 2-12, a mixture of HCMV-infected and uninfected NHDF cells (M.O.I.=0.001-0.002), i.e. 1-2 infected cells per 1000 uninfected cells. Row 12 (without substance) serves as virus control. The final test concentrations are 250-0.0005 µM. The plates are incubated at 37° C./5% CO₂ for 6 days, i.e. until all the cells are infected in the virus controls (100% cytopathogenic effect [CPE]). The wells are then fixed and stained by the addition of a mixture of formalin and Giemsa's dye (30 minutes), washed with double-distilled water and dried in a drying oven at 50° C. The plates are then assessed visually using an overhead microscope (plaque multiplier from Technomara).

The following data can be acquired from the test plates:

$CC_{50}$ (NHDF)=substance concentration in μM at which no visible cytostatic effects on the cells are evident compared with the untreated cell control;

$EC_{50}$ (HCMV)=substance concentration in μM which inhibits the CPE (cytopathic effect) by 50% compared with the untreated virus control;

SI (selectivity index)=$CC_{50}$ (NHDF)/$EC_{50}$ (HCMV).

Representative in vitro activity data of the compounds of the invention are shown in Table A:

TABLE A

| Example No. | NHDF $CC_{50}$ [μM] | HCMV $EC_{50}$ [μM] | SI HCMV |
|---|---|---|---|
| 1 | 11.0 | 0.019 | 579 |
| 28 | 18.0 | 0.0023 | 8032 |
| 29 | 47.0 | 0.01 | 4700 |
| 30 | 47.0 | 0.008 | 5875 |
| 36 | 24.0 | 0.005 | 6402 |
| 49 | 94.0 | 0.018 | 5222 |

The suitability of the compounds of the invention for the treatment of HCMV infections can be shown in the following animal model:

HCMV Xenograft Gelfoam® Model

Animals:

5-6-week-old immunodeficient mice (16-20 g), Fox Chase SCID.NOD or NOD.CB17-Prkdc/J, are purchased from commercial breeders (Taconic M&B, Denmark; Jackson, USA). The animals are kept under sterile conditions (including bedding and feed) in isolators.

Virus Growing:

Human cytomegalovirus (HCMV), Davis or AD169 strain, is grown in vitro on human embryonic prepuce fibroblasts (NHDF cells). After the NHDF cells have been infected with a multiplicity of infection (M.O.I.) of 0.01-0.03, the virus-infected cells are harvested 5-10 days later and stored in the presence of minimal essential medium (MEM), 20% foetal calf serum (FCS) (v/v), 1% glutamine (v/v), 1% Pen/Strep (v/v) with 10% DMSO at −80° C. After serial ten-fold dilutions of the virus-infected cells, the titre is determined on 24-well plates of confluent NHDF cells after fixing and staining with a Giemsa formaldehyde solution.

Preparation of the Sponges, Transplantation, Treatment and Evaluation:

Collagen sponges 1×1×1 cm in size (Gelfoam®; Peasel & Lorey, order no. 407534; K. T. Chong et al., Abstracts of 39$^{th}$ Interscience Conference on Antimicrobial Agents and Chemotherapy, 1999, p. 439) are initially wetted with phosphate-buffered saline (PBS), the trapped air bubbles are removed by degassing, and then stored in MEM, 10% FCS (v/v), 1% glutamine (v/v), 1% Pen/Strep (v/v). 1×10$^6$ virus-infected NHDF cells (infection with HCMV Davis or HCMV AD169 M.O.I=0.03) are detached 3 hours after the infection and added dropwise in 20 μl of MEM, 10% FCS (v/v), 1% glutamine (v/v), 1% Pen/Strep (v/v) to a moist sponge. The sponges are incubated for 3-4 hours to allow the cells to adhere. Then, following the addition of medium (MEM, 10% FCS) (v/v), 1% glutamine (v/v), 1% Pen/Strep (v/v)), the sponges are incubated overnight. For the transplantation, the immunodeficient mice are anaesthetized with Avertin or a ketamine/xylazine/azepromazine mixture, the fur on the back is removed using a shaver, the epidermis is opened 1-2 cm, unstressed and the moist sponges are transplanted under the dorsal skin. The surgical wound is closed with tissue glue or clips. 4-6 hours after the transplantation, the mice can be treated for the first time (one treatment is given on the day of the operation). On the subsequent days, oral treatment with substance is carried out three times a day (7.00 h and 14.00 h and 19.00 h), twice a day (8 h and 18 h) or once a day (9 h) over a period of 8 days. The daily dose is for example 1 or 3 or 10 or 30 or 100 mg/kg of body weight, the volume administered is 10 ml/kg of body weight. The substances are formulated in the form of a 0.5% Tylose suspension/PBS with 2% DMSO or another suitable mixture aiding solubility of the substances, e.g. 2% ethanol, 2.5% Solutol, 95.5% PBS. 10 days after transplantation and about 16 hours after the last administration of substance, the animals are painlessly sacrificed and the sponge is removed. The virus-infected cells are released from the sponge by collagenase digestion (330 U/1.5 ml) and stored in the presence of MEM, 10% FCS (v/v), 1% glutamine (v/v), 1% Pen/Strep (v/v), 10% DMSO at −140° C. Evaluation takes place after serial ten-fold dilutions of the virus-infected cells by determining the titer on 24-well plates of confluent NHDF cells after fixing and staining with a Giemsa formaldehyde solution. The number of infected cells or infectious virus particles (infectious centre assay) after the substance treatment compared with the placebo-treated control group is determined. Statistical evaluation takes place using suitable computer programs, for example GraphPad Prism.

C. Exemplary Embodiments of Pharmaceutical Compositions

The compounds of the invention can be converted into pharmaceutical preparations in the following ways:

Tablet:

Composition:

100 mg of the compound of Example 1, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of active compound, lactose and starch is granulated with a 5% solution (m/m) of the PVP in water. After drying the granulates are mixed with the magnesium stearate for 5 min. This mixture is compressed using a conventional tablet press (see above for the format of the tablet). A guideline for the compressive force used for the compression is 15 kN.

Suspension which can be Administered Orally:

Composition:

1000 mg of the compound of Example 1, 1000 mg of ethanol (96%), 400 mg of Rhodigel (xanthan gum from FMC, Pennsylvania, USA) and 99 g of water.

10 ml of oral suspension correspond to a single dose of 100 mg of the compound of the invention.

Production:

The Rhodigel is suspended in ethanol, and the active compound is added to the suspension. The water is added while stirring. The mixture is stirred for about 6 h until the swelling of the Rhodigel is complete.

Solution which can be Administered Intravenously:

Composition:

10-500 mg of the compound of Example 1, 15 g of polyethylene glycol 400 and 250 g of water for injection.

Production:

The compound of Example 1 is dissolved together with polyethylene glycol 400 in the water while stirring. The solution is sterilized by filtration (pore diameter 0.22 μm) and dispensed under aseptic conditions into heat-sterilized infusion bottles. The latter are closed with infusion stoppers and crimped caps.

What is claimed is:

1. A compound of formula

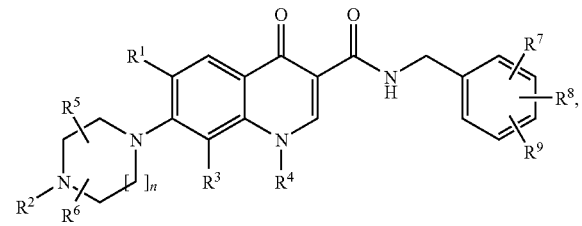

(I)

in which n represents a number 1 or 2, $R^1$ represents hydrogen, fluorine, chlorine or trifluoromethyl, $R^2$ represents $C_1$-$C_6$-alkyl, $C_1$-$C_6$-alkylaminocarbonyl or —C(=O)—$R^{10}$, whereby alkyl and alkylaminocarbonyl are substituted with a substituent, whereby the substituent is selected from the group consisting of hydroxy-carbonyl and $C_1$-$C_6$-alkoxycarbonyl, and $R^{10}$ represents hydroxycarbonyl, $C_1$-$C_6$-alkoxycarbonyl, hydroxycarbonylmethyl or $C_1$-$C_6$-alkoxycarbonylmethyl, $R^3$ represents halogen, cyano, methoxy, trifluoromethyl, monofluoromethoxy, difluoromethoxy, trifluoromethoxy or ethynyl, $R^4$ represents $C_1$-$C_6$-alkyl or $C_3$-$C_8$-cycloalkyl, whereby alkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkoxy, $C_1$-$C_4$-alkylamino, $C_1$-$C_6$-alkylcarbonyl and $C_1$-$C_6$-alkoxycarbonyl, and whereby cycloalkyl can be substituted with 1 to 3 substituents, whereby the substituents are selected independently of one another from the group consisting of halogen, hydroxy, amino, cyano, trifluoromethyl, hydroxycarbonyl, aminocarbonyl, $C_1$-$C_6$-alkyl, $C_1$-$C_6$-alkoxy, $C_1$-$C_6$-alkylamino, $C_1$-$C_6$-alkylcarbonyl and $C_1$-$C_6$-alkoxycarbonyl, or $R^3$ and $R^4$, together with the atoms to which they are bonded, form a ring through a group of formula

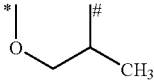

whereby

* is the linkage site to the carbon atom, and is the linkage site to the nitrogen acorn, $R^5$ and $R^6$ independently of one another represent hydrogen, methyl or ethyl, $R^7$ and $R^8$ independently of one another represent halogen, hydroxy, cyano, trifluoromethyl, monofluoromethoxy, difluoromethoxy, trifluoromethoxy, $C_1$-$C_3$-alkyl or $C_1$-$C_3$-alkoxy, $R^9$ represents hydrogen, halogen, hydroxy, cyano, trifluoromethyl, monofluoromethoxy, difluoromethoxy, trifluoromethoxy, $C_1$-$C_3$-alkyl or $C_1$-$C_3$-alkoxy, or one of its salts.

2. The compound of claim 1, corresponding to formula

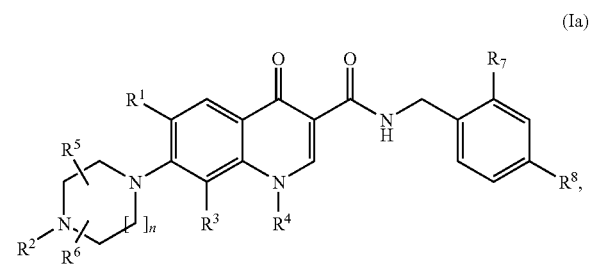

(Ia)

in which n represents the number 1, $R^1$ represents hydrogen or fluorine, $R^2$ represents $C_1$-$C_4$-alkyl, whereby alkyl is substituted with a substituent, whereby the substituent is selected from the group consisting of hydroxycarbonyl and $C_1$-$C_6$-alkoxycarbonyl, $R^3$ represents fluorine, chlorine, trifluoromethyl, methoxy, monofluoromethoxy, difluoromethoxy, trifluoromethoxy or ethynyl, $R^4$ represents $C_1$-$C_4$-alkyl or $C_3$-$C_5$-cycloalkyl, whereby alkyl can be substituted with 1 to 3 substituents, whereby the substituents are selected independently of one another from the group consisting of fluorine, hydroxy and $C_1$-$C_3$-alkoxy, and whereby cycloalkyl can be substituted with 1 to 3 substituents, whereby the substituents are selected independently of one another from the group consisting of halogen, hydroxy, trifluoromethyl, $C_1$-$C_3$-alkyl and $C_1$-$C_3$-alkoxy, or $R^1$ and $R^4$, together with the atoms to which they are bonded, form a ring through a group of formula

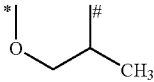

whereby

* is the linkage Site to the carbon atom, and is the linkage site to the nitrogen atom, $R^5$ and $R^6$ independently of one another represent hydrogen or methyl, $R^7$ and $R^8$ independently of one another represent fluorine, chlorine, cyano, trifluoromethyl, difluoromethoxy, trifluoromethoxy, $C_1$-$C_3$-alkyl or $C_1$-$C_3$-alkoxy, or one of its salts.

3. The compound of claim 1, corresponding to formula

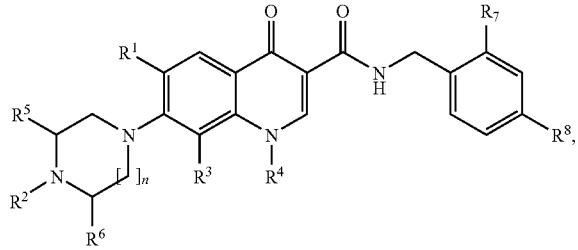

(Ib)

in which
n represents the number 1,
$R^1$ represents fluorine,
$R^2$ represents methyl or ethyl,
whereby methyl and ethyl are substituted with a substituent, whereby the substituent is selected from the group Consisting of hydroxycarbonyl, methoxycarbonyl and ethoxycarbonyl,
$R^3$ represents chlorine, methoxy, difluoromethoxy or trifluoromethoxy,
$R^4$ represents methyl, ethyl or cyclopropyl,
whereby ethyl can be substituted with 1 to 3 fluorine substituents,
and
whereby cyclopropyl can be substituted with 1 to 2 fluorine substituents, or
$R^3$ and $R^4$, together with the atoms to which they are bonded, form a ring through a group of formula

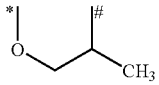

whereby
* is the linkage site to the carbon atom,
and
is the linkage site to the nitrogen atom,
$R^5$ and $R^6$ independently of one another represent hydrogen or methyl,
$R^7$ and $R^8$ independently of one another represent chlorine, trifluoromethyl, trifluoromethoxy or methyl,
or one of its salts.

4. A method for preparing a compound of formula (I) of claim 1, wherein a compound of formula

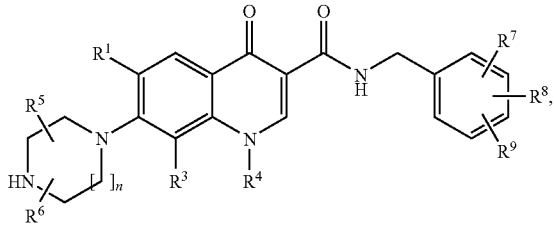

(II)

in which
n, $R^1$, $R^3$, $R^4$, $R^5$, $R^6$, $R^7$, $R^8$ and $R^9$ have the meaning indicated in claim 1, is reacted, according to method [A], with a compound of formula $$R^2-X^1 \quad (III),$$

in which
$R^2$ represents $C_1$-$C_6$-alkyl,
whereby alkyl is substituted with a substituent $C_1$-$C_6$-alkoxycarbonyl and
$X^1$ represents halogen, preferably iodine, chlorine or bromine, or mesylate, tosylate or triflate,
or
according to method [B], with a compound of formula $$R^{2a}-NCO \quad (IV),$$

in which
R2a represents the alkyl of the alkylaminocarbonyl of the radical R2,
whereby alkylaminocarbonyl is substituted with a substituent $C_1$-$C_6$-alkoxycarbonyl,
or
according to method [C], with a compound of formula

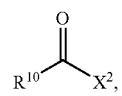

(V)

in which
$R^{10}$ has the meaning indicated in claim 1,
and
$X^2$ represents halogen,
or
whereby a compound formed by the reaction of a compound of formula (II) with a compound of formulae (III) or (IV)
is hydrolysed, according to method [D], with a base to form the corresponding acid.

5. The method of claim 4, wherein $X^1$ represents iodine, chlorine, bromine, mesylate, tosylate, or triflate.

6. The method of claim 4, wherein $X^2$ represents chlorine or bromine.

7. A medicament comprising a compound of claim 1 in combination with an inert, non-toxic, pharmaceutically acceptable excipient.

8. A method for the production of a medicament for the treatment, prophylaxis or treatment and prophylaxis of viral infections using a compound of claim 1, comprising combining a compound of claim 1 with an inert, non-toxic, pharmaceutically acceptable excipient.

9. A method for treating infections with the human cytomegalovirus or another representative of the group of herpes viridae in humans and animals by administering an antivirally effective amount of at least one compound of claim 1.

10. A method for treating infections with the human cytomegalovirus or another representative of the group of herpes viridae in humans and animals by administering an antivirally effective amount of at least one compound of claim 7.

11. A method for treating infections with the human cytomegalovirus or another representative of the group of herpes viridae in humans and animals by administering an antivirally effective amount of at least one medicament obtained according to the method of claim 8.

* * * * *

UNITED STATES PATENT AND TRADEMARK OFFICE
CERTIFICATE OF CORRECTION

PATENT NO. : 7,569,563 B2
APPLICATION NO. : 12/006086
DATED : August 4, 2009
INVENTOR(S) : Kai Thede et al.

It is certified that error appears in the above-identified patent and that said Letters Patent is hereby corrected as shown below:

On the Cover Page:

Item (30), "10 2005 030 524" should be -- 10 2005 030524.5 --.

At Column 75, lines 54-55, "$C_1$-$C_4$-alkylamino" should be -- $C_1$-$C_6$-alkylamino --.

At Column 77, line 25, "Consisting" should be -- consisting --.

At Column 78, lines 8-9, "halogen, preferably iodine, chlorine or bromine, or mesylate" should be -- halogen, mesylate --.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,569,563 B2  Page 1 of 1
APPLICATION NO. : 12/006086
DATED : August 4, 2009
INVENTOR(S) : Kai Thede et al.

It is certified that error appears in the above-identified patent and that said Letters Patent is hereby corrected as shown below:

At Item (73), "AiCuris GmbH & Co. HK" should be -- AiCuris GmbH & Co. KG --.

Signed and Sealed this

Twenty-seventh Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,569,563 B2
APPLICATION NO. : 12/006086
DATED : August 4, 2009
INVENTOR(S) : Kai Thede et al.

It is certified that error appears in the above-identified patent and that said Letters Patent is hereby corrected as shown below:

Title Page, Item (73) Assignee, "AiCuris GmbH & Co. HK" should be -- AiCuris GmbH & Co. KG --.

This certificate supersedes the Certificate of Correction issued July 27, 2010.

Signed and Sealed this

Twenty-fourth Day of August, 2010

David J. Kappos
*Director of the United States Patent and Trademark Office*